(12) United States Patent
Weissman

(10) Patent No.: US 7,234,940 B2
(45) Date of Patent: Jun. 26, 2007

(54) COMPONENTS FOR PERMANENT REMOVABLE AND ADJUSTABLE DENTURES AND BRIDGES

(76) Inventor: Bernard Weissman, 225 E. 48th St., New York, NY (US) 10017

( * ) Notice: Subject to any disclaimer, the term of this patent is extended or adjusted under 35 U.S.C. 154(b) by 386 days.

(21) Appl. No.: 10/746,674

(22) Filed: Dec. 24, 2003

(65) Prior Publication Data

US 2004/0166476 A1    Aug. 26, 2004

Related U.S. Application Data

(60) Provisional application No. 60/504,922, filed on Sep. 22, 2003, provisional application No. 60/436,890, filed on Dec. 27, 2002.

(51) Int. Cl.
*A61C 13/02* (2006.01)
(52) U.S. Cl. .................... 433/168.1; 433/173
(58) Field of Classification Search ............... 433/173, 433/174, 168.1
See application file for complete search history.

(56) References Cited

U.S. PATENT DOCUMENTS

| | | | | |
|---|---|---|---|---|
| 711,324 | A * | 10/1902 | Lacy ................... | 433/173 |
| 1,101,810 | A * | 6/1914 | Otrich et al. ......... | 433/177 |
| 2,112,007 | A * | 3/1938 | Adams ................. | 433/174 |
| 3,085,334 | A * | 4/1963 | Bischof et al. ....... | 433/180 |
| 3,514,858 | A | 6/1970 | Silverman ............ | 433/174 |
| 3,656,236 | A * | 4/1972 | Kurer ................... | 433/221 |
| 3,748,739 | A | 7/1973 | Thibert ................ | 433/173 |
| 4,204,321 | A * | 5/1980 | Scott ................... | 433/177 |
| 4,253,834 | A * | 3/1981 | Staubli ................. | 433/173 |
| 4,290,755 | A * | 9/1981 | Scott ................... | 433/173 |
| 4,459,111 | A | 7/1984 | Valen .................. | 433/176 |
| 4,516,937 | A | 5/1985 | Bosker ................. | 433/173 |
| 4,654,006 | A * | 3/1987 | Kusano et al. ....... | 433/168.1 |
| 4,787,851 | A * | 11/1988 | Kusano et al. ....... | 433/173 |
| 4,854,872 | A | 8/1989 | Detsch ................. | 433/173 |
| 5,052,928 | A | 10/1991 | Andersson .......... | 433/183 |
| 5,052,930 | A | 10/1991 | Lodde et al. ........ | 433/173 |
| 5,064,374 | A | 11/1991 | Lundgren ............ | 433/173 |
| 5,194,000 | A * | 3/1993 | Dury ................... | 433/173 |
| 5,427,906 | A | 6/1995 | Hansen ............... | 433/173 |
| 5,513,988 | A * | 5/1996 | Jeffer et al. ......... | 433/168.1 |
| 5,520,540 | A * | 5/1996 | Nardi et al. ......... | 433/172 |
| 5,538,428 | A | 7/1996 | Staubli ................ | 433/173 |
| 5,567,155 | A | 10/1996 | Hansen ............... | 433/173 |
| 5,575,651 | A | 11/1996 | Weissman ........... | 433/173 |
| 5,597,306 | A * | 1/1997 | Horlitz et al. ....... | 433/173 |
| 5,678,993 | A * | 10/1997 | Jeffer et al. ......... | 433/168.1 |
| 5,725,376 | A | 3/1998 | Poirier ................ | 433/172 |
| 5,788,492 | A | 8/1998 | Weissman ........... | 433/173 |
| 5,871,357 | A * | 2/1999 | Tseng .................. | 433/189 |

(Continued)

*Primary Examiner*—Ralph A. Lewis
(74) *Attorney, Agent, or Firm*—Paul J. Sutton; Barry G. Magidoff

(57) ABSTRACT

A dental prosthesis foundation capable of being finished or adjusted or repaired and which may be assembled and adjusted to variable jaw ridge sizes, and formed with self-curing hardened resins. The foundation supports prosthetic teeth and is permanently but removably secured to the jaw by implants embedded in hard dental tissue, such as tooth stubs or bones. The dentures can be readily repaired or adjusted for changes in the jaw of the patient, by chairside techniques available to dentists. The foundation can also be adjusted to changes in size and shape of ridges in the jawbones for more comfortable use of the dentures secured on such prostheses.

21 Claims, 19 Drawing Sheets

U.S. PATENT DOCUMENTS

| | | | |
|---|---|---|---|
| 5,885,077 A * | 3/1999 | Jeffer | 433/168.1 |
| 6,068,479 A * | 5/2000 | Kwan | 433/173 |
| 6,382,975 B1 | 5/2002 | Poirier | 433/173 |
| 6,575,742 B2 * | 6/2003 | Kyung et al. | 433/18 |
| 6,685,473 B2 | 2/2004 | Weissman | 433/173 |
| 6,716,030 B1 * | 4/2004 | Bulard et al. | 433/174 |

* cited by examiner

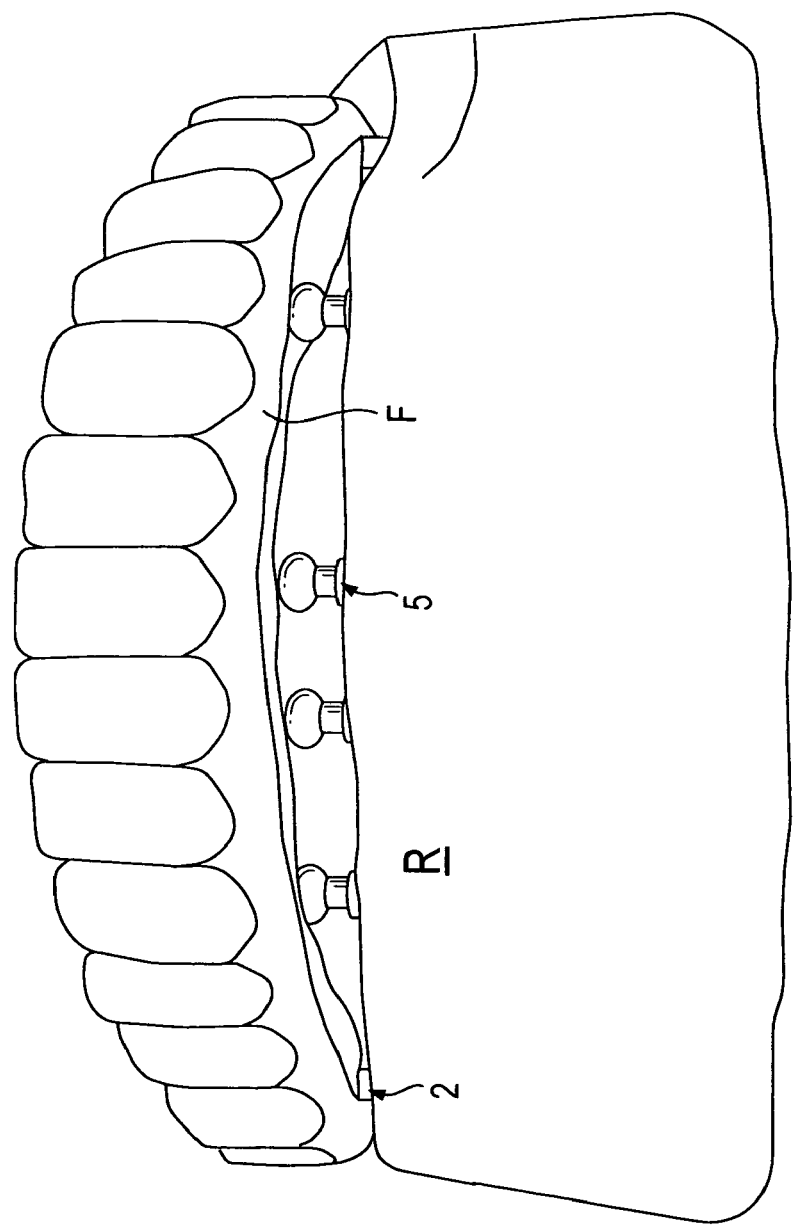

COMPONENTS FOR PERMANENT REMOVABLE AND ADJUSTABLE DENTURES AND BRIDGES

This application claims priority pursuant to 35 U.S.C. 119(e) from U.S. provisional patent application Ser. No. 60/436,890 filed Dec. 27, 2002 and Ser. No. 60/504,922 filed Sep. 22, 2003, and pursuant to 35 U.S.C. 120 from copending U.S. application Ser. No. 09/970,475 filed Oct. 4, 2001, now U.S. Pat. No. 6,685,473.

CROSS-REFERENCE TO RELATED APPLICATIONS

This invention provides further improvements to, and is related to, U.S. patent application Ser. No. 09/970475, filed Oct. 4, 2001, the complete disclosure of which is incorporated herein by reference, including the specification, drawings and claims.

FIELD OF THE INVENTION

The present invention relates to further improvements in dental implant structures, and in particular to adjustable and/or modular, removably secured dentures and dental bridges, i.e., oral, or dental prosthetics. A detailed background for this invention is provided in related U.S. patent application Ser. No. 09/970475, filed Oct. 4, 2001, by the same inventor, now U.S. Pat. No. 6,685,473, the complete disclosure of which may be incorporated herein by reference, including the specification, drawings and claims (hereinafter the "Prior Case").

BACKGROUND OF THE INVENTION

As shown in FIG. 1 of the Prior Case, it is well known to firmly attach dentures to hard dental tissue, such as the jawbone 14 or tooth stubs by an implanted support, via prosthetic dental bridges 10; foundations 12 for such bridges 10 are known. In particular, the dental bridge 10 may be securely mounted to implanted screw posts 16, or other known securing mechanisms. Such foundations 12 are also described, for example, in U.S. Pat. Nos. 5,575,651 and 5,788,492. Other, more readily removable, dentures secured to implanted supports are shown, for example in U.S. Pat. Nos. 5,567,155 and 3,514,858.

The relatively slender implants to support foundations described in the first two patents identified above, and in the Prior Case, were originally considered suitable primarily as short term devices for use until the larger, "permanent" implants healed. One aspect of the present invention continues the earlier development and understanding that the slim implants can be used for substantially permanent, but removable denture prostheses of various types. The devices and procedures of the present invention avoid many of the problems of earlier systems when worn for extended periods, which included the lack of capability for easy removal and replacement, and potential irritation to the patient because of the difficulty of obtaining a proper fit to the jawbone and opposing teeth and gums, or to soft dental tissue.

Thus, a need continued to exist for a system which would permit the placement of a long-lasting dental prosthesis in a patient's mouth by chairside techniques available to the family dentist. Such a system should provide components for mounting such prosthesis, which can be firmly secured to the hard dental tissue, such as the jawbone, in a relatively short time, but which can be adjusted or removed to be prophylactically cleaned or repaired at a later date, and which is readily adaptable to the natural variations in the size and shape of ridges in jaw bones, so as to provide for more comfortable use of any dentures secured on such components.

Certain patients also find it preferable to be able to remove their dentures for daily cleaning. Problems arise with such readily removable systems, however, if a patient's jawbone continues to erode, or otherwise change, under the denture, or the internal portion of the denture is deformed from aging or lengthy use, resulting in a loose fit, lack of function and irritation to the patient's jaw. It is a common practice to bore out and reline existing or new dentures, which were originally made to rest on the gum, and to be retained by a close fit, without the alternative of using a denture adhesive, requiring reapplication each day. In all cases it is important that the denture continue to be accurately retained in the precise position in the jaw, especially relative to the opposing teeth. Any lining or relining must maintain the same or improved fit and retention, by firmly connecting the denture to implanted screws in the identical position regarding the prosthetic teeth.

SUMMARY OF THE INVENTION

In accordance with a first aspect of the present invention, the channel forming the concave underside of a full, or partial, denture, for either the upper or lower jaw, can be lined with a resilient material, covering the hard denture form, and thus more effectively maintain the denture in the correct position while cushioning the patient's dental ridge. Such a denture lining is intended to provide for an improved grip on implants, and can be readily resurfaced. Furthermore, the existing or new denture can be retrofitted with the advantageous system of this invention. The prosthesis can be removed from the mouth by the patient to be prophylactically cleaned daily, or resurfaced at a later date by the dentist, and is readily adaptable to the natural variations in the size and shape of ridges in jawbones, so as to provide for more comfortable use of any dentures including such components.

In a first improvement, in addition to the anchoring implants, indexing guide pins are provided that are permanently implanted, bi-laterally, at the most posterior parts of the jaw. Such indexing pins can be the usual screw-type titanium dental implant device screwed into the jawbone and extending upwardly through and beyond the gum, to provide an indexing pin extending above the gum. A matching enlarged index aperture is provided in the bottom channel of the denture to ensure a precise alignment of the denture with the positioning pins. A hard, preferably metallic, indexing sleeve is permanently affixed in the denture, to prevent abrasion and misalignment each time the indexing pin moves into or out of the aperture. An example of such an indexing sleeve is shown resting on an indexing pin, before emplacement in a denture, in FIG. 2. The retaining implants preferably now have a spheroidal head extending above the gum line, and a platform substantially at the gum line and connected the spheroidal head by a slender neck.

A chairside prosthesis foundation is also provided for securing to a plurality of anchored dental implants, in accordance with the Prior Case. Each implant useful in that situation has an intermediate platform portion and an inter-connectable top distal from the preferably threaded, implanted portion. The foundation can comprise modular components, which can be supported by the intermediate implant platforms, but which can be locked together by being encased in a resin, in a permanent relative juxtaposition. The locked together components can be removably connected to the implants, to enable subsequent adjustment of the prosthesis to fit a range of jaw ridge sizes or for cleaning or repair. As explained in the Prior Case, such modular components are secured in the jaw efficiently and relatively easily, and can be adjusted at a later date, to conform to the many variations in the size or shape of ridges in the jaw, rendering the prostheses more comfortable to the wearer. As also explained in the Prior Case, the modular components can be interconnected while secured to the implants and are then reinforced and locked together by being encased by a cured, or hardened, resin composition, such as any of the self-curing dental resins well known to dentists.

Both types of foundations, each referred to as a "splint", provides a base upon which tooth forms/synthetic teeth can be supported. When the screw shafts are implanted, temporary tooth forms can be created at chairside by a dentist, once a splint is in place, to provide a patient with a prompt replacement of missing teeth, which are firmly but replacably connected to the implants, aiding the healing of the implants to the bone. Immediately after placing the implants, the splint serves to index the implanted screws so that they are maintained in position without movement, to aid in the healing process and to allow the bone to firmly grow around the implants.

During the initial healing process, it is desirable to avoid movement or dislodgement of the implanted screws resulting from the normal motions of the mouth and tongue. To achieve this, the implant screws are locked in place, together, by providing the splint. In one embodiment, shown in the Prior Case, each implant shaft has a polygonal top driving portion, engaging an indexing member which fits around and is held in a desired juxtaposition by the polygonal top. The preferred indexing member has paired arms extending outwardly therefrom, forming slots there between. Connecting bars, or flexible bands, extend through the slots on each indexing member from the first of a series of such implants to the last of the series, thus interconnecting the indexing members and thus anchoring the group of implanted screws together, to support each other in the desired juxtaposition. Each indexing member is in turn releasably secured to its respective implant shaft by a locking cap. To further enhance the rigidity and support provided by the overall splint structure, the bars and the indexing members are encased in a resinous material, thus forming a unitary rigid structure, which can be separated as a unit from the series of implants. In accordance with the improvement of the present invention, by forming the locking caps from a material non-adherent to the encasing dental resin, such as silicone or other polymeric non-adherent material, such as the polyacetal Delrin, the locking cap can be readily unscrewed from the implant, so that the foundation splint structure can be removed from the implants, once the implants are firmly set, i.e., fully healed to the bone. Either of the temporary or longer term dentures can by supported on, and connected to the splint.

BRIEF DESCRIPTION OF THE DRAWINGS

FIG. 8 illustrates a front view of a splint being applied to the jaw, over the holding implants.

DETAILED DESCRIPTION OF THE PREFERRED EMBODIMENTS

Figure 1:
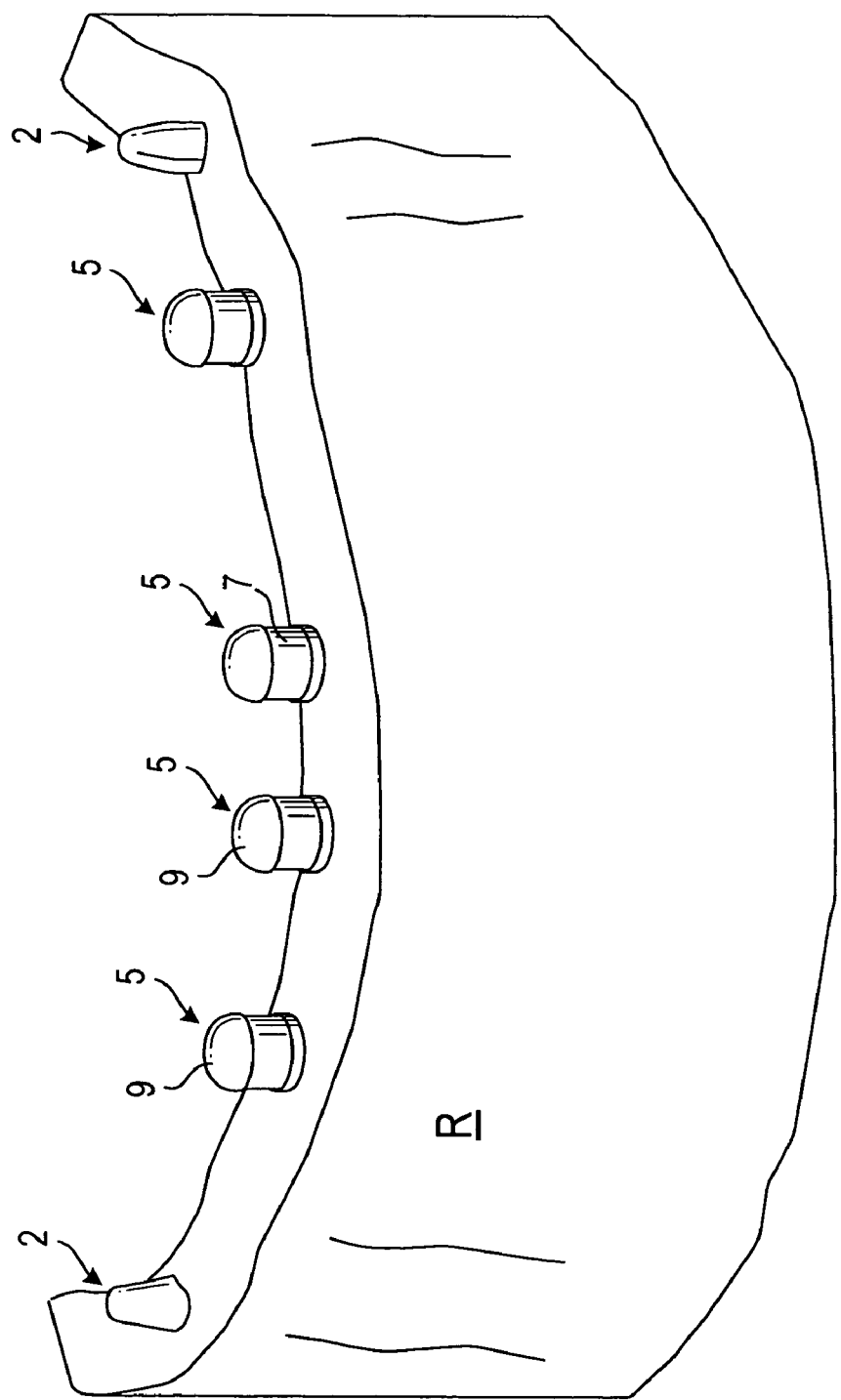
FIG. 1 illustrates, on a jaw model, a series of indexing and holding implants having the desired spheroidal head of this invention and banded necks.

As described herein, the various rigid structural components shown in the drawings are fabricated from, for example, titanium, stainless steel, and/or any other suitable dental implant material which can withstand functional loads and support crowns, bridge segments, or the complete replacement of teeth with tooth forms/synthetic teeth/artificial teeth.

Figure 1A:
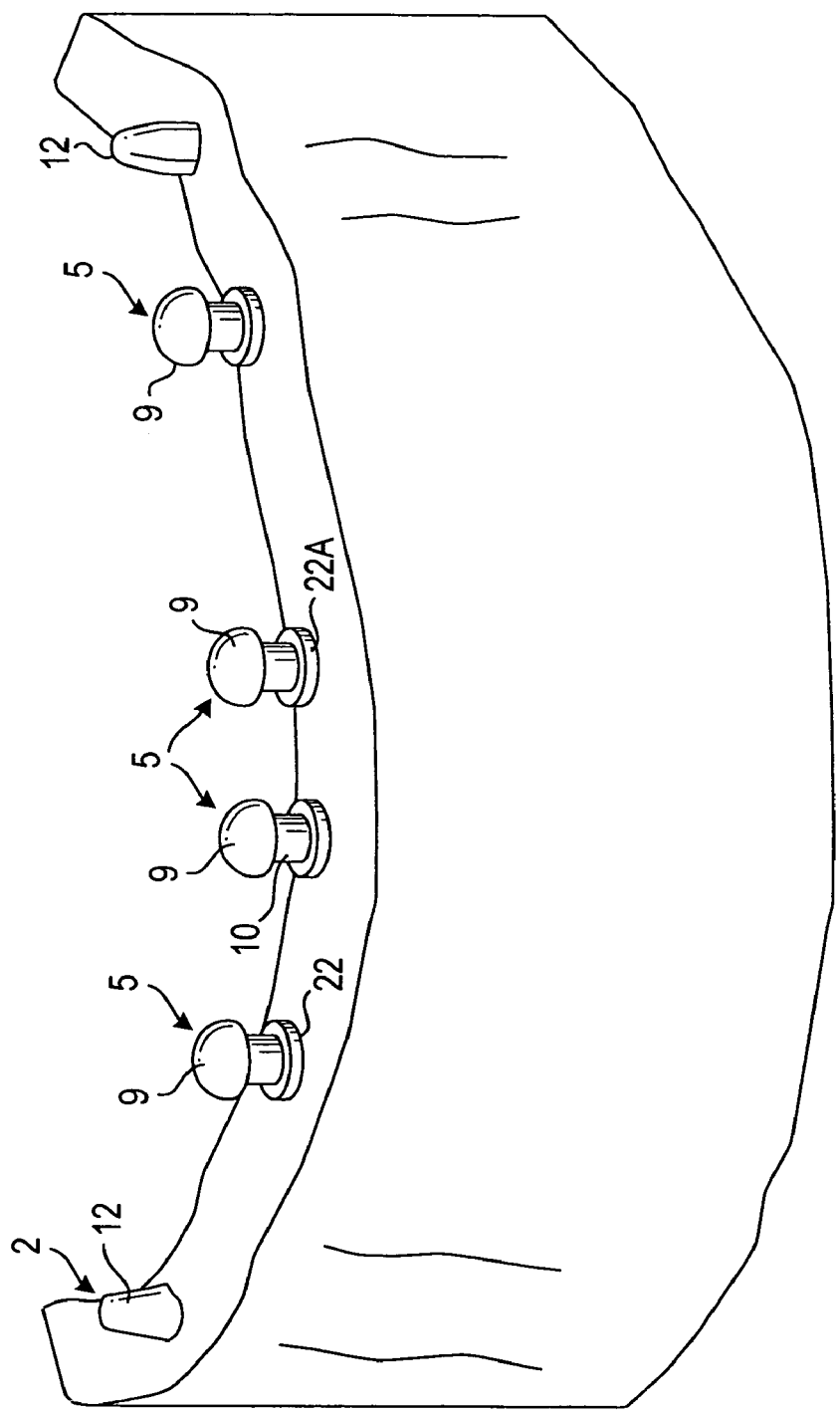
FIG. 1a illustrates, the jaw model of FIG. 1, of a series of indexing and holding implants having the desired spheroidal head of this invention without the neck bands.

A model of a patient's jaw ridge R is shown in FIGS. 1 and 1a, including implanted into the jawbone ridge a pair of the guide, or indexing, pins 2 in the posterior-most portions of the model, and a series of implant screw type retention pins 5. Each of the retention pins has a flattened dome-shaped, or spheroidal, head 9, and a narrower neck 10 and threaded shank 20, extending into the jawbone. Intermediate the shank and neck is a flange 22 having a distally facing platform 22A. The combination of the neck 10 and head 9 provides an undercut surface for retention and the platform 22A a firm support for the denture. In addition, as will be explained further below, closely surrounding the neck 10 there may be employed a removable elastic band 7, which can be utilized to vary the degree of any undercut effect by reducing or increasing the effective diameter of the shank to the needs of the patient.

Figure 5:
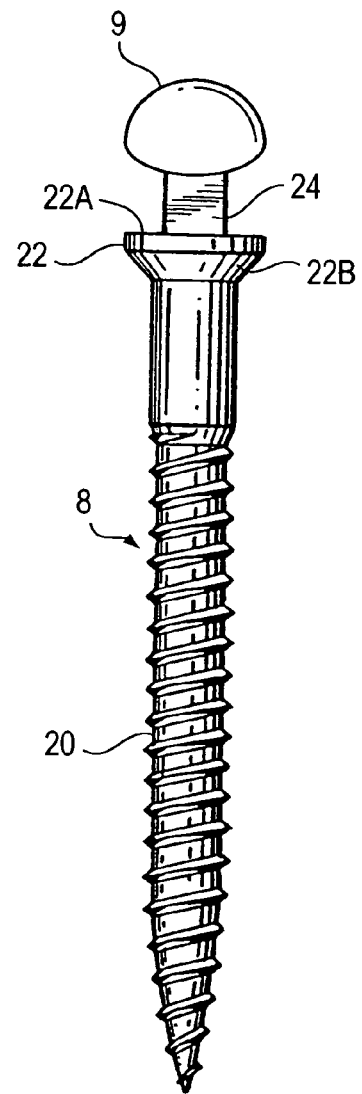
FIG. 5 illustrates an elevation view of a spheroidal headed implant for the present invention, as shown in FIG. 1.
Figure 7:
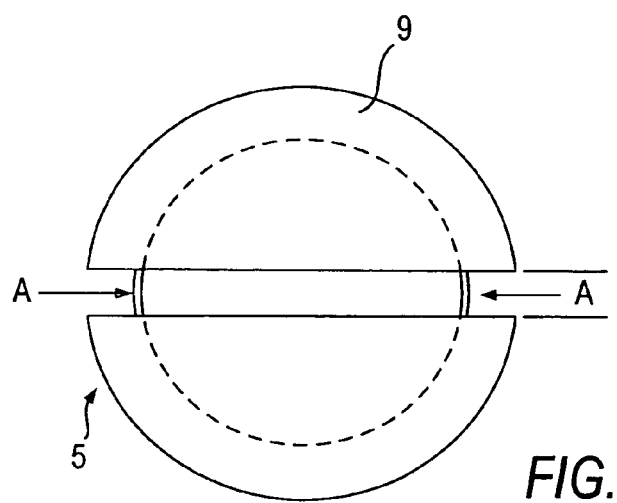
FIG. 7 illustrates a top plan view of the spheroidal head of the holding implants shown in FIG. 5.

The head 9 is preferably a flattened sphere, having a circular transverse cross-section, i.e., in the plan view of FIG. 5, but an ovoid cross-section when viewed along the axial plane of the implant shaft, i.e., the elevation view of FIG. 7, and having, e.g., a slot 37 serving as a driving portion, as shown in FIG. 5 The driving portion 37 is adapted to engage a tool, such as, in this example, a screw driver, which may be manually or mechanically driven, such as by a dental drill, to turn the screw 5 in a selected rotational direction to secure or remove the screw 18 from the hard dental tissue, in a manner known in the art. The screw 5 can thus be anchored in the ridge portion of e.g., the jawbone in a self-threading manner.

The advantage of the flattened spheroid is that it does not extend axially as far as a full sphere of the same diameter, but at the same time, it provides the continuous smooth surface which is least likely to be uncomfortable to the wearer and also simplifies dental hygiene by avoiding any sharp corners. The spheroidal headed implant can be used for a single tooth prosthesis (FIG. 11) or as part of a bridge denture, with other such implants. A slot 37 may also be provided in the head, to permit easier insertion of the implant into the jaw.

Figure 11:
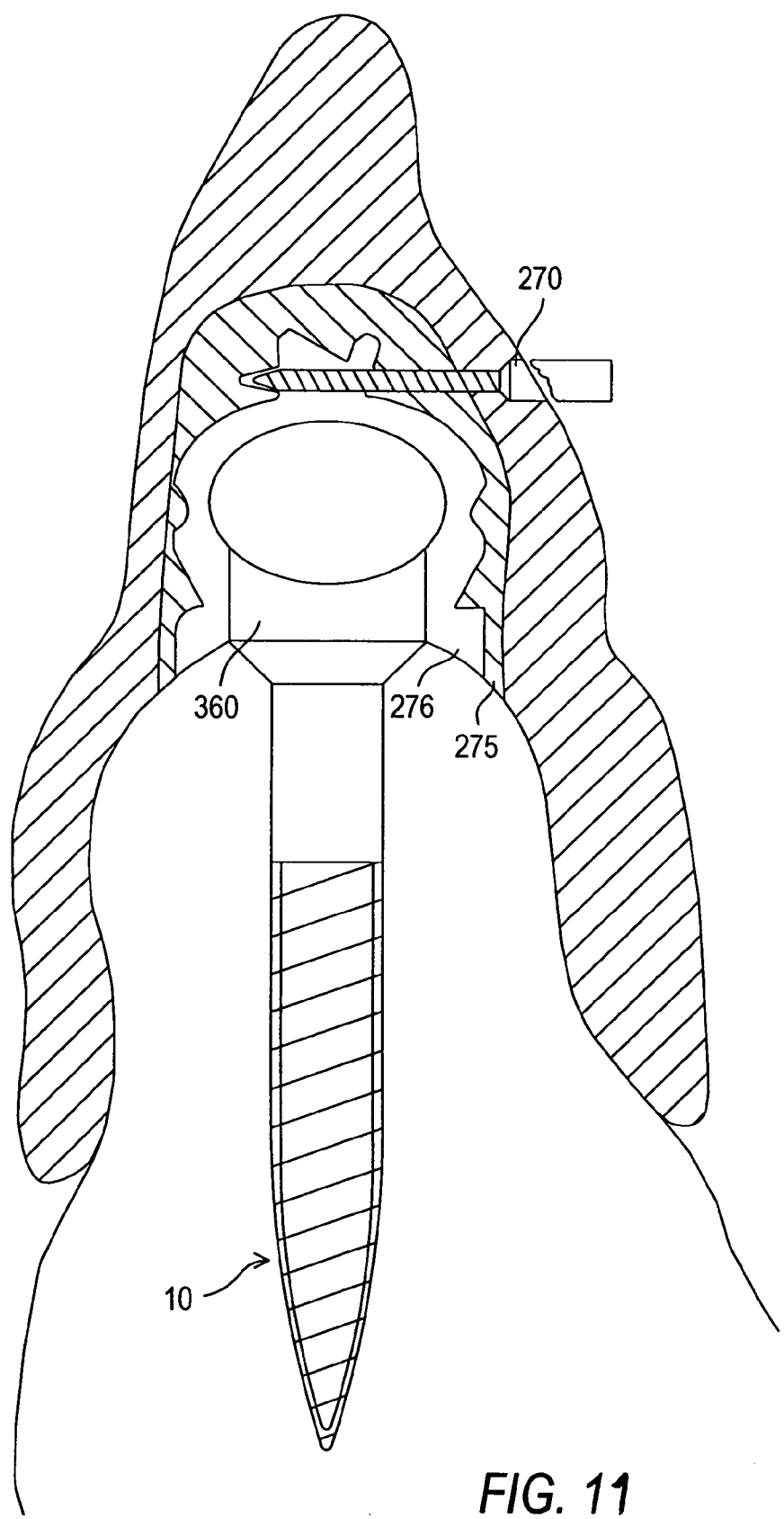
FIG. 11 is a cross-sectional elevational view of a single tooth prosthesis anchored to an implant.

As shown specifically in FIG. 11, and described more fully in the context of the Prior Case, another preferred embodiment of the holding implant screw 94, 18 has, at one end, a relatively long self-tapping threaded shaft 20. In use, an opening is made through any soft dental tissue, e.g., gums, overlying the jawbone, and the implant screw 18 is screwed into the hard dental tissue. The implant screw 18 has various advantageous features, such as a flange 22, functioning as an implant platform, having a flat surface 22A on a first side adjacent to which modular components are positioned and supported, and having a tapered smooth portion 22B on a second side facing the dental tissue from which the threaded shaft 20 extends. The threads preferably do not extend the full length of the shaft 20, such that a substantially smooth, unthreaded portion is preferably present immediately adjacent the tapered portion 22B. In addition, this embodiment of the implant screw 18 includes a driving portion 24 which, in this example, is a flat polygonal extension, having a rectangular longitudinal cross-section. The driving portion 24 is adapted to engage a tool, such as a socket wrench bit. This is more fully set out in the Prior Case, incorporated herein. It is understood that the driving portion need not be in the specific shape shown, and may be polygonal concavity or extension, to engage compatible tools known in the art.

Figure 12:
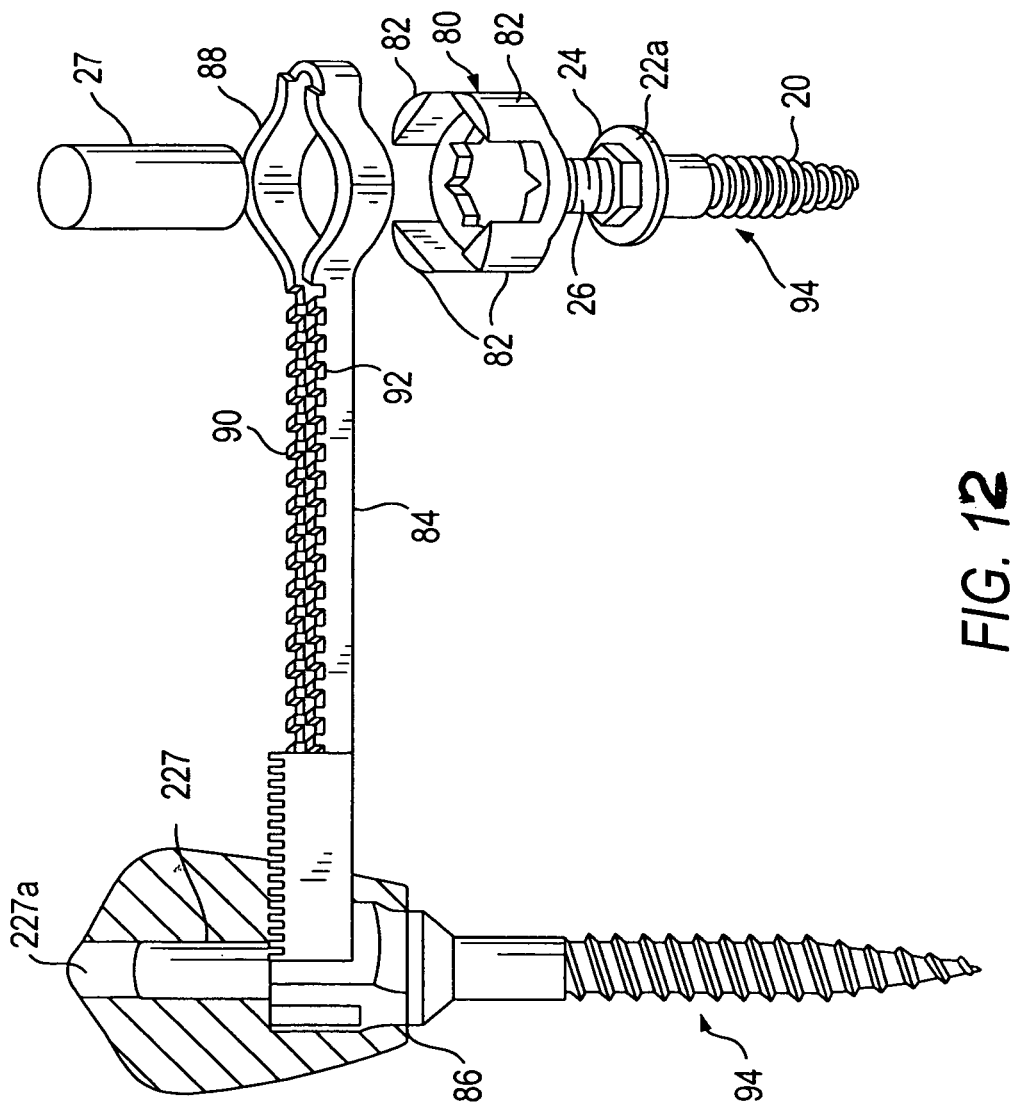
FIG. 12 illustrates the skeleton of a prosthesis foundation which is threadedly connected to the implants.

This second preferred embodiment of the slender holding implant screw 94, as shown in FIG. 12 includes at the protruding longitudinal end, another type of prosthesis connecting member 26 for attaching the modular prosthesis components thereto. In the preferred embodiment of FIGS. 2-5, the prosthesis connecting member 26 is externally threaded, as shown most clearly in FIG. 2, for receiving an internally threaded cap 27; (an embodiment of a cap is shown in FIG. 10), for removably but rigidly connecting the implant screw to the splint.

The implanting of the relatively slender indexing implant pins 2 is the same as is discussed above, for example, with respect to the holding implant pins. It is noted that unlike the relatively slender holding, or retention, pins 5, the upper or outer portion of the indexing pins 12, preferably taper inwardly towards the end distal of the gum line.

All of the implanted pins in the several embodiments of the present invention are preferably formed of titanium metal (or alloys thereof can also be used), having threaded shank diameters in the range of preferably 1.6 to 2.1 millimeters, preferably not greater than about 2 mm, and an overall length of at least about 16 millimeters and preferably not more than about 20 millimeters. The threaded shanks are substantially the same for both the indexing and holding pins.

Figure 10:
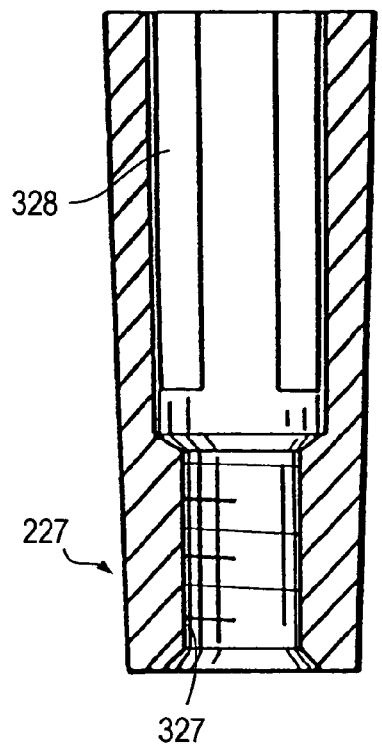
FIG. 10 illustrates a locking screw cap made of a structural, nonadherent polymer, such as the polyacetal Delrin, to secure the prostheseis to the implant.

As shown in FIGS. 10 and 12, the present invention also provides for a locking screw cap 227, made of a structural, nonadherent polymer, which can be used to secure the splint to the above described second implant embodiment. The Delrin screwcap 227 can have the same structure as one made of titanium, i.e., an internal threaded portion 327 at one end, and an internal preferably polygonal circumferential driving surface 328 at the other end. The advantage of this type of screw cap 227 is that it is less likely to cause any damage to the relatively fragile threaded upper portion 26 of the implant (which may be caused by, e.g., cross threading or overtightening a cap screw made of a relatively hard metal, such as titanium) or to the denture material, because of e.g., Delrin's relative softness, flexibility or elasticity, relative to the material forming the implant, and at the same time it is non-adherent to the more common dental resins, used to encapsulate the splint. This nonadherent, polymer cap 227 is also tapered inwardly, towards the internally threaded end 327, so as to ease removal when being unscrewed after the hardening of the resin around the polymer cap 227. The cap 227 preferably also has an internal polygonal drive portion 328, at the end distal from the, preferably internal threaded, connection to the implanted shaft. The tightly holding, hardened resin, is preferably of the type which swells slightly as it sets and hardens, thus pressing against the locking cap to the implant, such as the polymeric, e.g., Delrin, cap or against the spheroidal head of an implant, thus serving to further reinforce the structure, by either preventing any slippage of the relatively soft and flexible plastic Delrin cap on the implant threads, after the resin has hardened, or firmly gripping the spheroidal head when the splint is applied.

Prior to initially forming the splint, of whichever form, a mold of the mouth showing the locations of the upper ends of the implants and their shape, together with any indexing element 80 present on each implant, is made using the usual dental impression material. A denture prosthesis can be prepared from this mold, by known procedures, which will locate the implant tops extending through the dental prosthesis. The concavity formed by the posterior indexing implants should be expanded to a larger opening to leave room for the jacket insert to be attached to the denture. This initial foundation, formed from a relatively hard dental resin, is then treated to remove material from the concave portion formed around the jaw ridge, to permit the molding of a softer more resilient dental resin liner, as follows.

Figure 2:
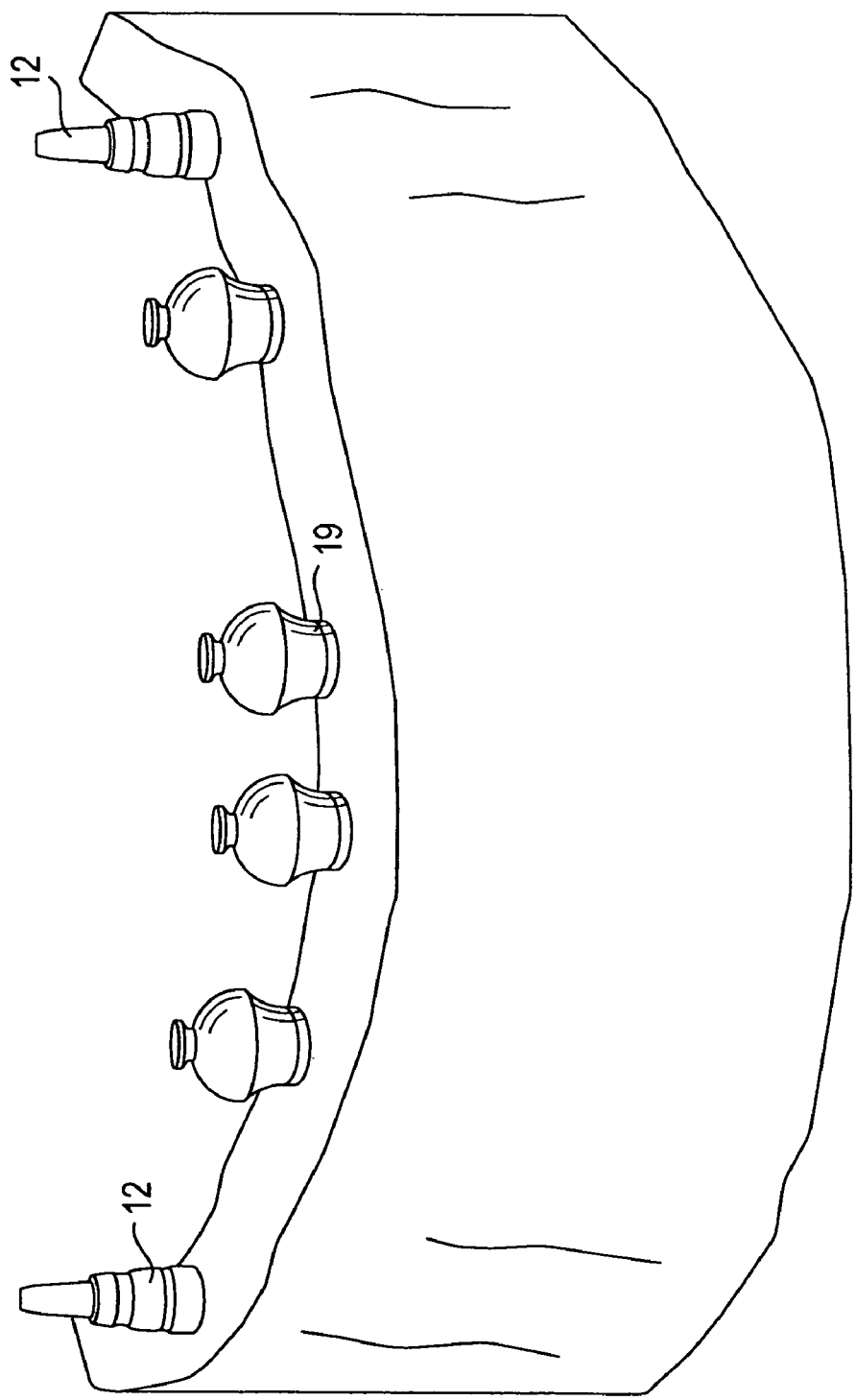
FIG. 2 illustrates, the jaw model of FIG. 1 with insert covers over the indexing implants.

In FIG. 2, it is shown that the exposed portions of the holding pins 5, prior to molding the dental foundation insert, can also be covered by removable jackets 19, which are preferably formed of a silicone dental resin, and are to be permanently imbedded in the final denture to provide a more durable contact surface for the holding pin 5. As shown, the jackets 19 extend over and around undercut portions of the spheroidal head 9, to improve their retention in the denture and to reduce the likelihood of their being withdrawn when the dentures are removed from the mouth. By molding the jackets 19 into the denture liner when originally fabricating the liner, the denture can be readily removed, portions of the material forming the denture channel surface are cut-out and relined in situ, by the dentist. The denture is then readily replaceable in a precise location in the jaw by virtue of the pins 2 in the indexing sleeves 12, which remain firmly attached in place. The sleeves 12, are imbedded in the hard denture material, are not worn away by removing the denture from over the indexing pins 2, thereby extending substantially the life of the denture by permitting accurate repeated resurfacing in spatial position and height to match the opposing teeth, in the event of changes to the jaw ridge or wearing of the portions surrounding the spheroidal holding pins.

By providing for a permanent spatial indexing of the denture in the jaw, aligned with the opposing teeth, the further advantages of the present invention overcome the need of prosthodontic specialists to establish anew the important gnatalogioal parameters each time the denture is relined.

As shown in FIG. 2, a flexible, preferably resilient, jacket, made, e.g. of a silicone dental polymer, or other resilient resin can be placed over the spheroidal top of the holding implant. As explained, this avoids any adhesion between the curing resin and the implant surface permitting ready removal of the denture after the resilient denture material is cured. The silicone or other polymeric resilient sleeve need not be non-adherent to the dental resin placed in the denture channel, for the in situ molding to the dental ridge. Nonadherency may be desirable, if it would enable ready replacement of the jacket in the event of wear, reducing the frequency of remolding the denture channel liner. The silicone sleeve can be easily picked out from the resin in the denture when it is removed from the jaw, or maintained in place.

After having formed the relatively hard internal portion of the denture, which will retain the guide sleeve 12 for the indexing pins 2, the remaining portions of the concave denture channel can be enlarged and filled with a self-curing resilient dental resin to permit the formation of a comfortable contact between the gum and the denture, even in those circumstances where due to age or illness, the jawbone ridge has become very thin. When preparing an older, existing denture to be modified to utilize the system of the present invention, or a new denture foundation, a relatively large channel is made in the denture for passive position alignment. First, a denture material is hard cured at least in the posterior portions of the channel, so as to permanently place the guide sleeves 12 in the rear portions of the denture. Once the sleeve is accurately placed and the hard resin cured, the remaining steps can follow in a routine manner.

Figure 3:
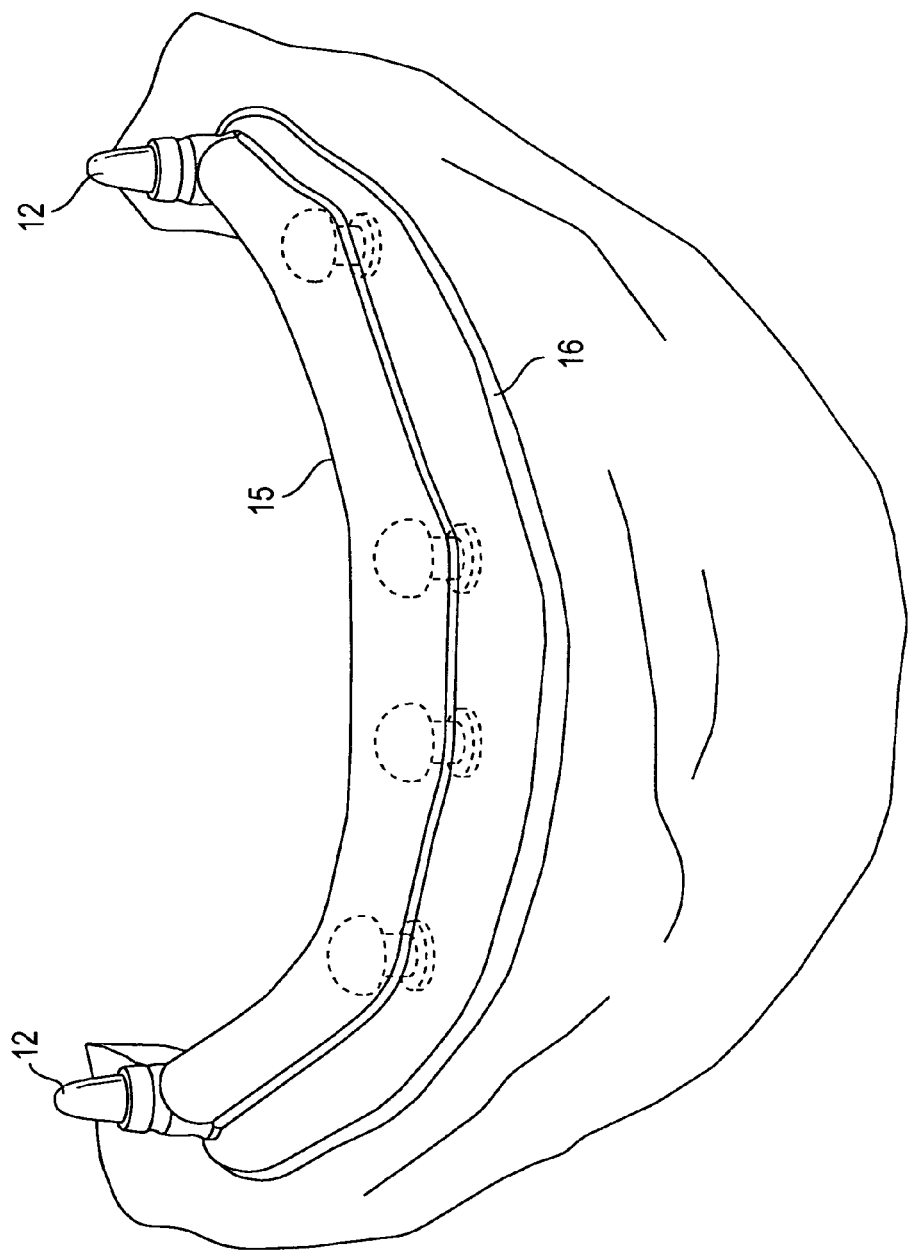
FIG. 3 illustrates, the jaw model of FIG. 1; wherein the holding implants are covered by a half sheath.
Figure 4:
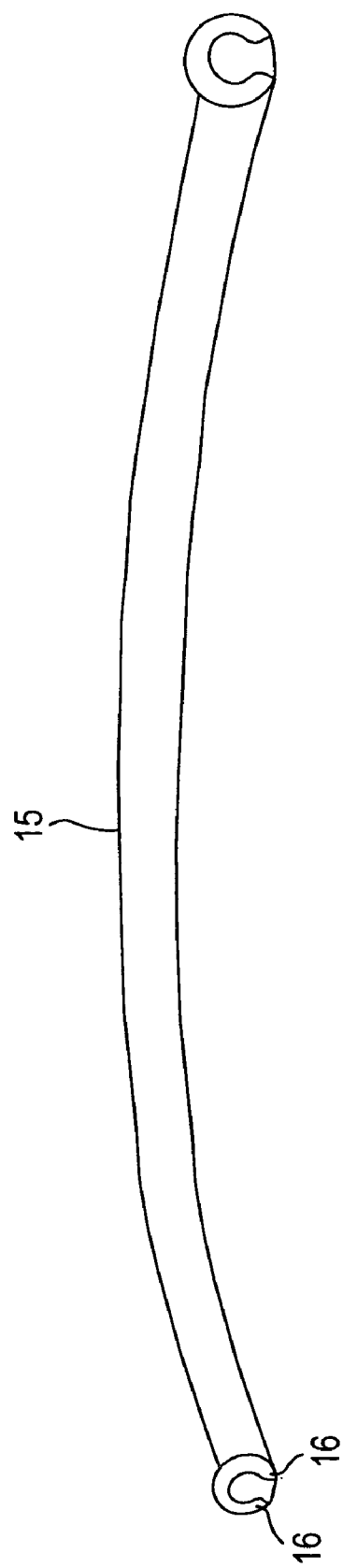
FIG. 4 illustrates a detailed perspective view of the half sheath shown in FIG. 3.

In a preferred process, a soft partial tube indicated by the numeral 15 in FIG. 3, is placed along the jaw ridge over the spheroidal caps but preferably ending adjacent the guide pins. The soft semi-tube channel has a preferably "Omega-shaped" cross-section, rather than forming a true semi-circle or simple partial oval. The cross-section of the tube 15 is shown in FIG. 4. The tube is so sized that the ends 15A of the Omega-shaped cross-section contact the surface of the relatively small diameter shank of the implant keeper, below the dome. When the denture filled with the curable dental resin is placed over the gum, the resin will cure in the shape of the tube; thereby forming the indented channel encasement, along the entire edge of the denture base. Thus, when a denture is placed in the jaw such that the guide pins extends into the indexing sleeve and the keeper pins extend into the channel, there will be an elastic effect where the interior of the channel, into which the domed-shaped heads will fit, has a larger diameter than the opening, thereby serving improve the retention of the denture on the jaw. There is thus a resilient surface on the interior of the denture providing a cushioning effect to the jawbone increasing the comfort of the wearer, while simultaneously acting to improve the retention of the denture in the mouth, thereby avoiding any embarrassing loss of dentures during use, such as while eating.

Figure 6:
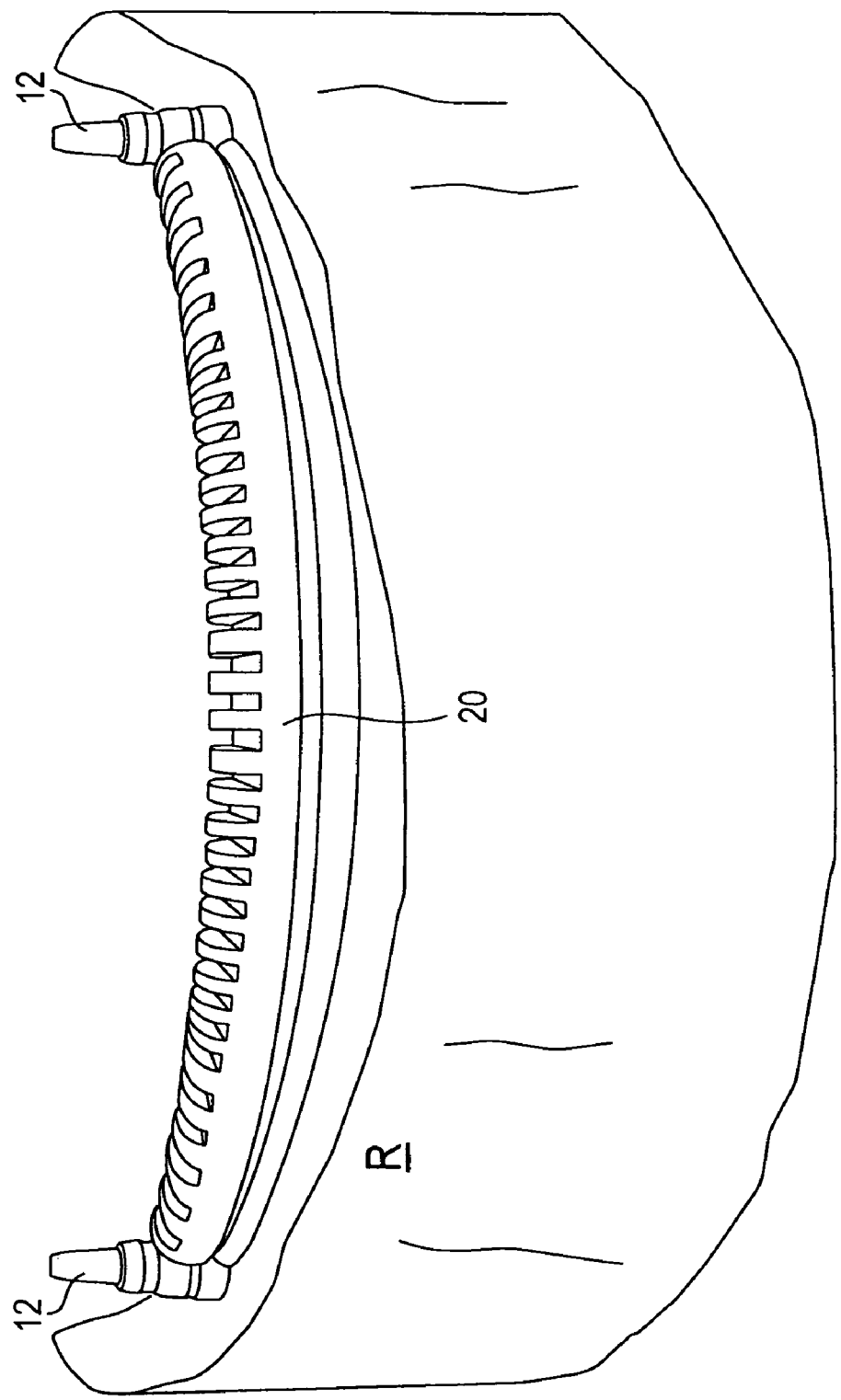
FIG. 6 illustrates, the jaw model of FIG. 3, wherein the holding implants are covered by a half sheath which is in turn covered by a metal reinforcing frame.

The Omega-shaped tube 15 can be formed of a material, which is non-adherent to the dental resin and therefore would be easily removed when the dental resin is fully cured.

Where it is required to deeply grind-out the interior of a denture to make sufficient space for the liner, the denture may be sufficiently weakened to require a metal reinforcement. Such reinforcement can be provided by the slotted metal shield 20 shown in FIG. 6. The metal strip is sufficiently flexible that it can be fitted over the silicone tube 15 and follow the curvature of the jawbone. When the resilient curable resin is placed in the hollowed-out denture and the denture placed over the metal shield, the curable resin will flow through the slots thereby filling the entire space between the sleeve and the silicone tube thereby forming a laminated metal resin reinforced structure with sufficient rigidity and strength.

The comfort of the patient when using a denture can be further enhanced by originally molding a denture with flanges that extend around the jawbone ridge. To enhance proper fit and comfort, and to reduce the likelihood of material inserting itself between dentures and gum, a pair of channels are formed on either side of the denture flange, which are filled with the any resilient material as the upper portion, and thus form a seal and a comfortable cushioning along ridge and the lower edge of the denture. A silicone small diameter bead space is formed on a replica of the jaws that firmly retains a resurfacing liner in place. The liner is removable for home care use an easily replaced in its indexed predetermined position, providing a patient with optimum hygiene and comfort.

It is recognized that it may be desirable to reduce the stress required to remove denture from the domed-shaped pins, for those persons who don't require a very firm fit for their dentures and would prefer to more easily remove the denture every evening for cleaning or soaking for any reason. The providing of resilient bands that can be stretched to fit over the dome and wrapped tightly around the neck of each of the pins, provides a means to adjust the degree of undercut, thus reducing the stress required to remove the denture from the retaining pins. These resilient bands can be of varying thickness to permit gradations in the effect of the resilient resin griping the domed-shaped pins. Examples of such bands are shown in FIG. 9E, in place around the shank of the pin. A simple pair of needle-nose pliers can be used to spread the band so as to fit over the spheroidal dome and then left in place around the shank. Similarly because of the softness of that resin, if it is desired to remove the band they can be readily sliced.

As a final advantage, it is possible to form a simple silicone, tooth-colored denture replacement, frictionally retained by the instant implants, for night time sleep use. These would not be suitable for chewing but would allow the patient to remove the denture without having to sleep, or otherwise, with the bare pins exposed.

The implant of this invention having a spheroidal head, as in FIG. 10, is effective for use for a single tooth prosthesis or as part of a bridge denture, where one or more of the spheroidal caps are placed on the implants As shown in FIGS. 5 and 11, an internal hollowed out portion, such as a groove or cup, is formed on the bottom of the denture. The groove or cup is filled with, e.g., a self-cure polymerizing resin 275, and a prefabricated silicone wafer 276 is affixed over the spheroidal cap 360, and the underside of the denture, with the resin, is pressed down over the silicone covered spheroidal cap. The silicone wafer 276 does not adhere to the curing resin 275, but the resin frictionally holds the silicone covered spheroid after the resin sets. The denture can be pulled off from the spheroidal cap by virtue of the inherent elasticity of the resin and the silicone. If desired to render the denture not removable by the patient, the prosthesis can be locked in place, which would also prevent it from accidentally coming loose, by a cross-pin 270 extending from the interior (labial side) of the prosthesis into the silicone wafer 276 through the resin 275. When the cross-screw 270 is removed, the prosthesis then can be flexibly pulled off.

One example of a preferred procedure for forming a single full denture plate e.g. for a lower jaw, is set forth in FIGS. 9A through 9I. The process is shown in terms of a model of a patient's jaw ridge depicted in each of the figures but most fully presented in FIG. 9A. This denture is of the patient removable type but intended to be long term and thus substantially permanent. The advantage is that if there is a problem with, for example, food particles being pushed between the denture and the jaw, the patient can remove and clean the denture himself, or jaw ridge can be cleaned and rested from further irritation while any irritation heals. This system makes this possibly by providing the permanent spatial indexing of the denture in the jaw by virtue of the implanted screws.

Figure 9A:
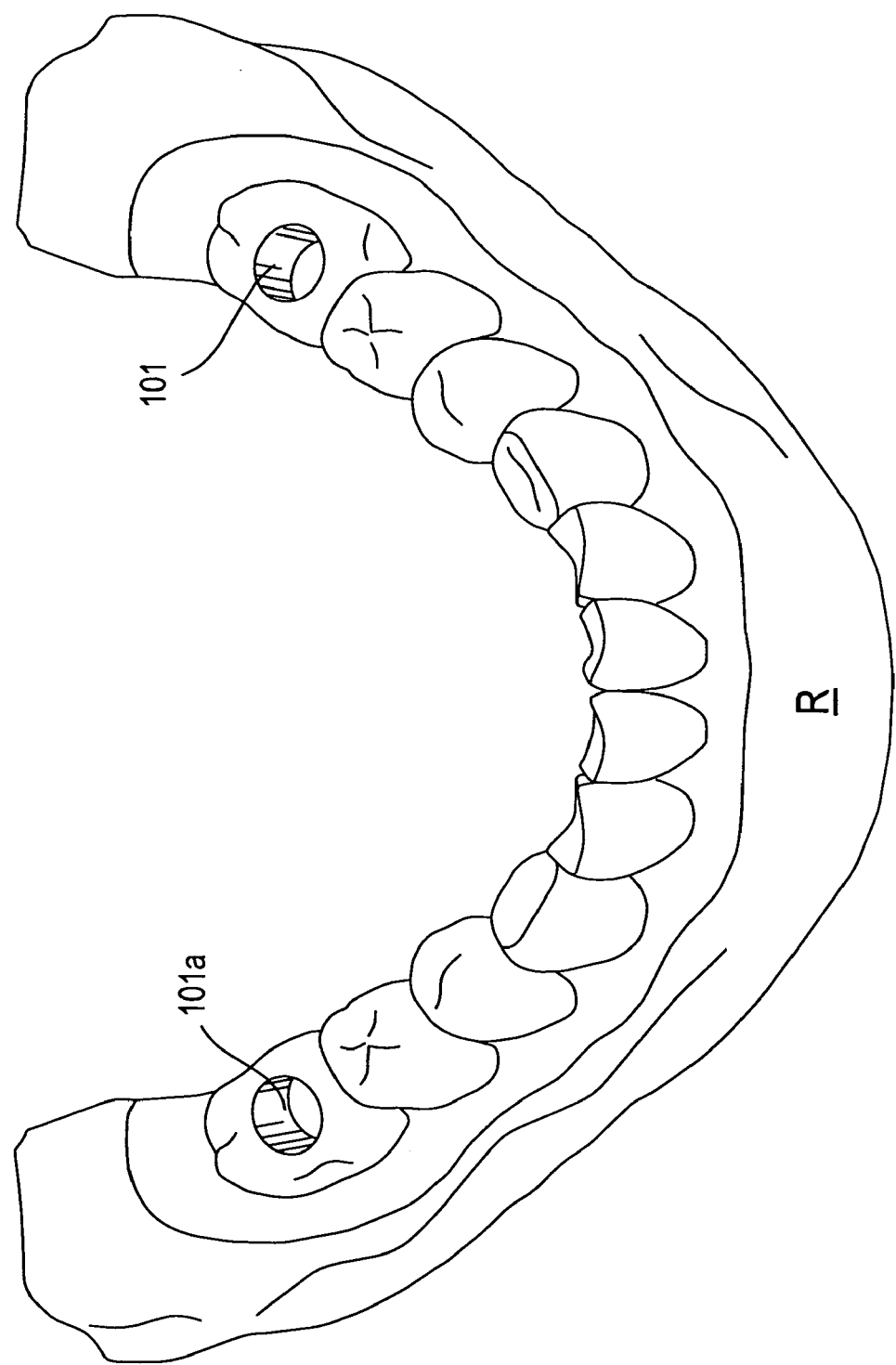
FIGS. 9A-I illustrate the procedure for forming a completed splint or dental prosthetic bridge in accordance with the present invention.
Figure 9B:
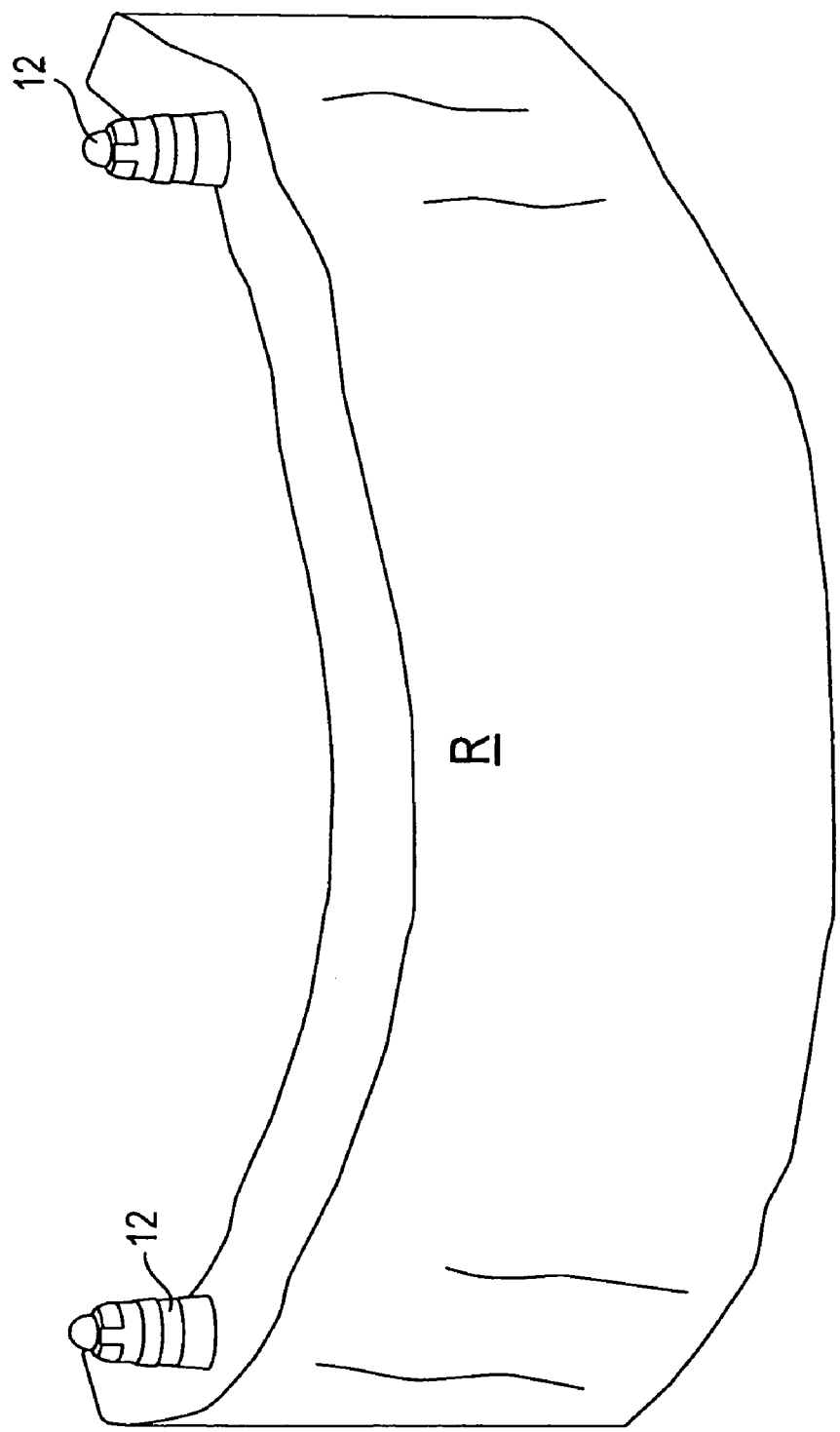

Referring to FIG. 9A, there is a pair of enlarged openings provided in the most distal parts of the denture for locater implants, as shown by the openings 101 at the rear molar locations. As shown in FIG. 9B, a pair of positioning implants 2 is set at the rear-most positions in the jaw bone R, and complimentary openings 101, 101a to match, are set in the prospective dentures. In FIG. 9B, the positioning implants 2 are shown covered by sleeves 12, or copings, which are to be secured into the denture and into which the locater implants 2 will slide when the denture is in place. By so doing, as explained above, wear of the denture material is minimized, as the sleeve 12 is formed of a low friction durable material which would not as readily wear as the hard denture material. In addition, the material of the sleeve 12 can also have sufficient flexibility and resilience to provide further cushioning with respect to the locater implants.

Figure 9C:
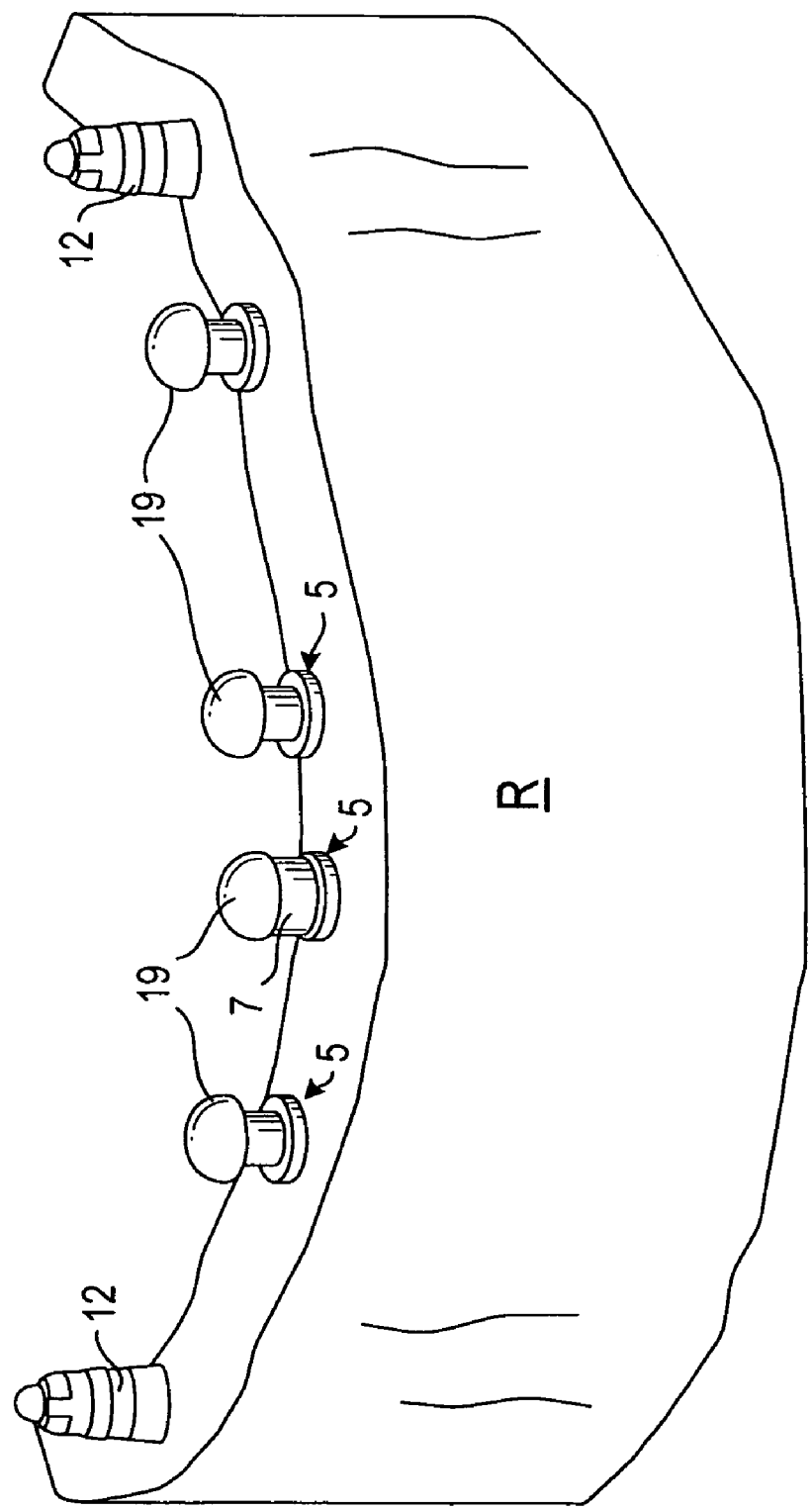

FIG. 9C depicts the jaw bone ridge after the holding implants 9 have been screwed into place in the jaw bone. These holder implants 18 have the overall appearance shown in FIG. 5 or 10. The implant 18 may have a removable spheroidal top, 361, if desired for any reason. As shown in FIG. 9C, color-coded elastic resilient bands 7 may be placed on the neck of each of the holder implants 18 to reduce the undercut between the neck portion and the major diameter of the spheroid top 9. As explained above, this allows for variability in the force required to remove a denture from the implants. A thicker band 7 reduces such force, and thus the strain on the denture, whereas the maximum force would be required when there is no band in place. FIG. 9E displays the use of a special sphere-like tool, for expanding the resilient bands to fit them over the major diameter of the spheroid cap when placing them around the neck of the implant.

Figure 9D:
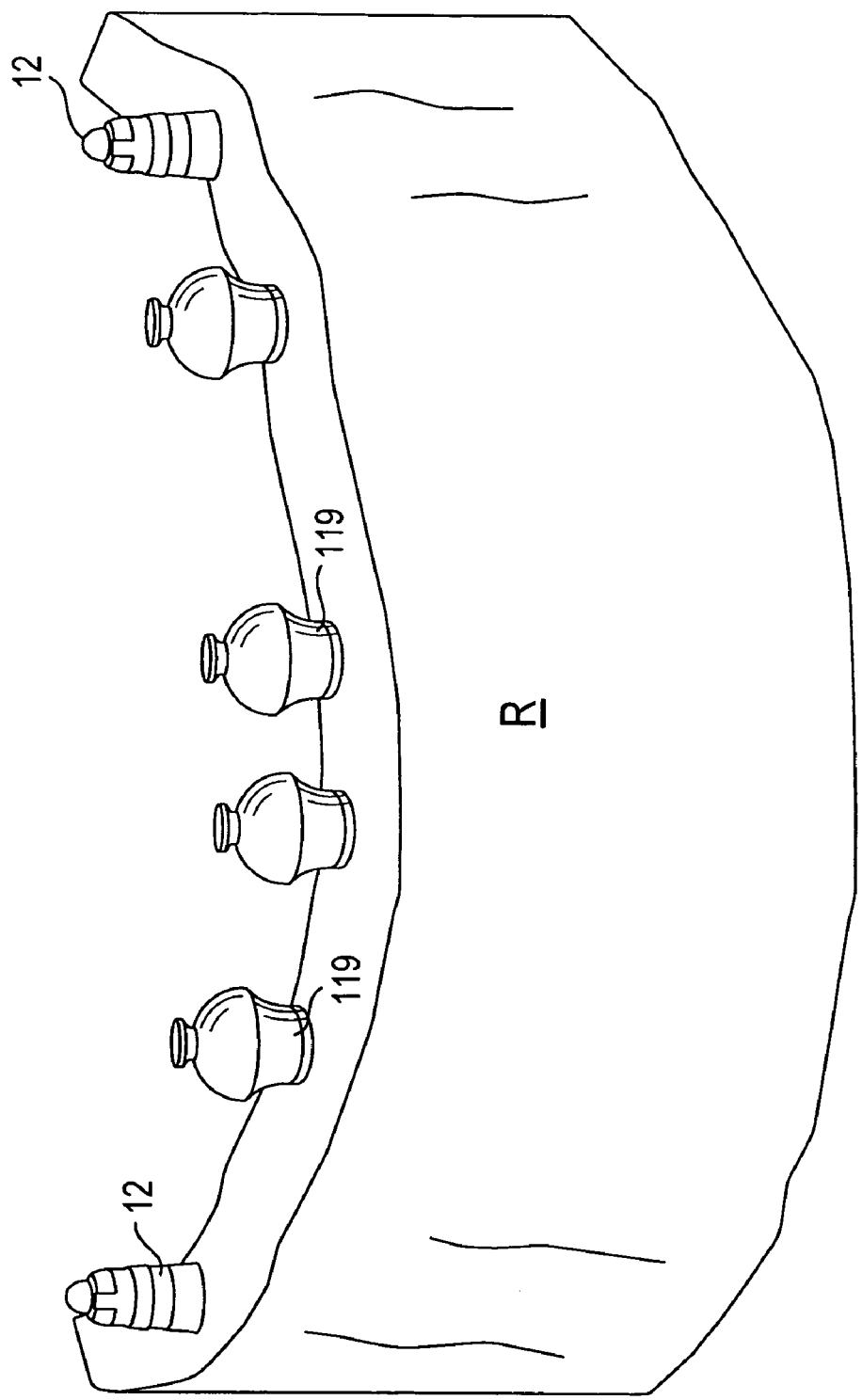
Figure 9E:
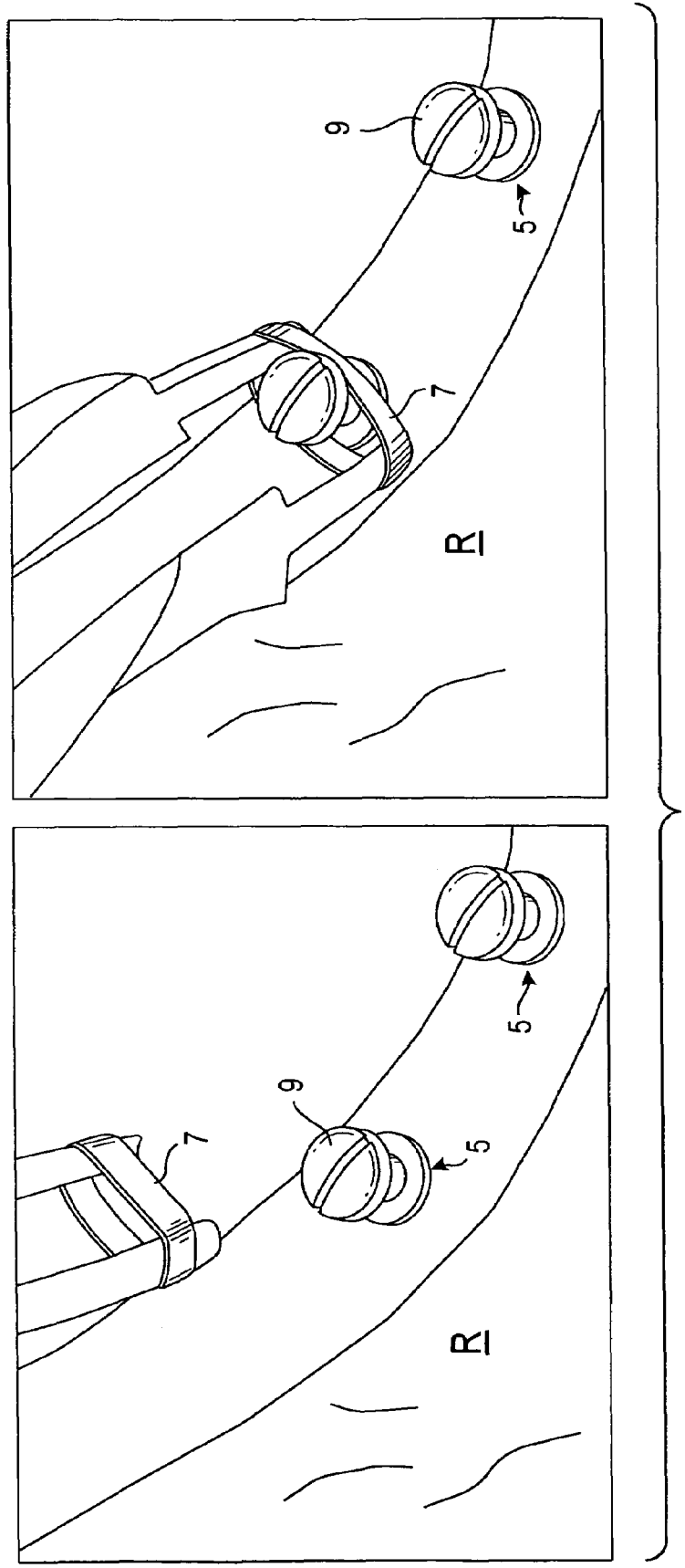

FIG. 9D shows the same view as 9C, but snap-on silicone caps 119 are in place over the spheroid top 9 of each implant 18. Again as explained above, these resilient caps provide means for avoiding any adhesion between a curable dental resin and the metal surface of the spheroid top.

Figure 9F:
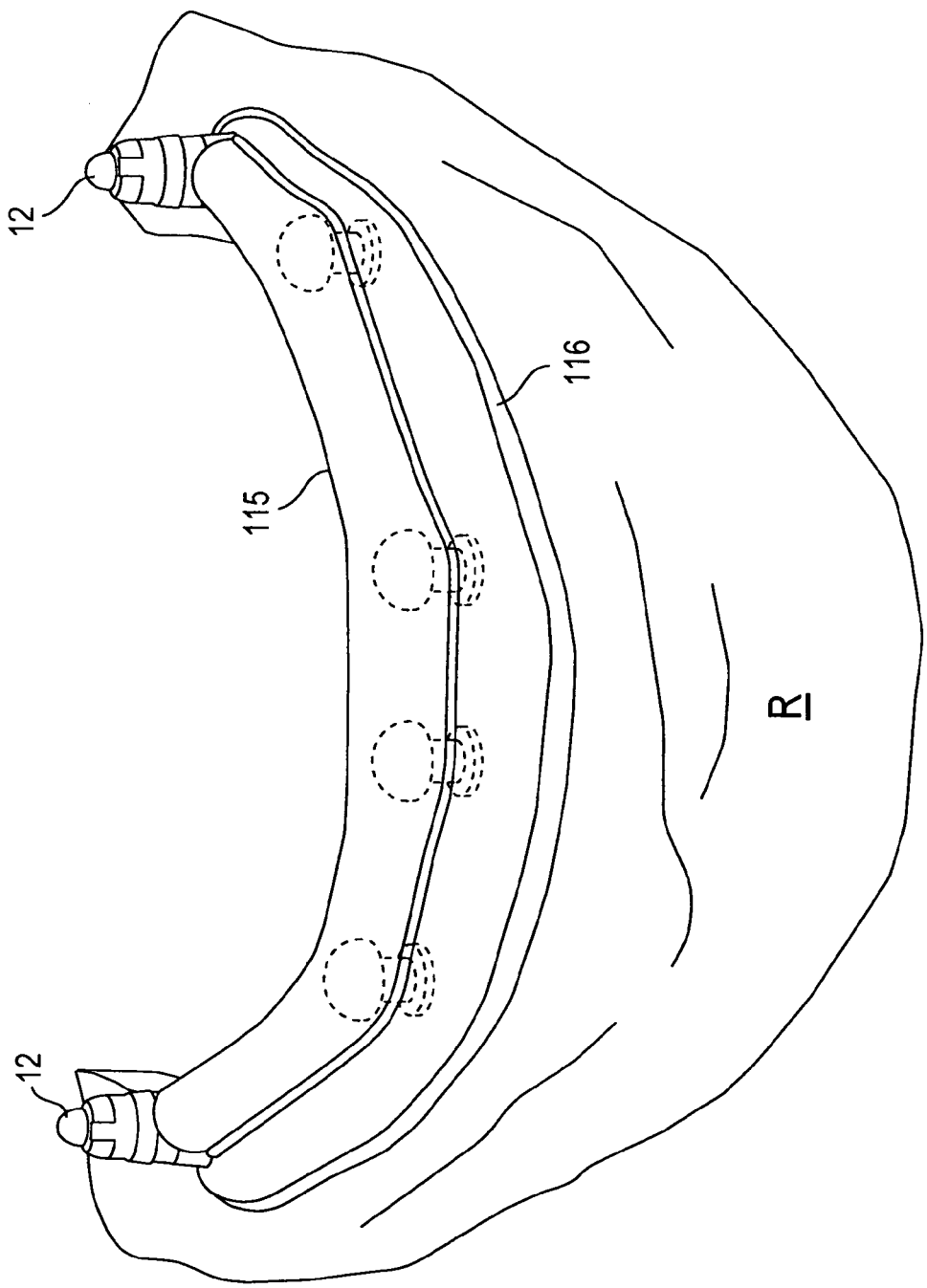

In the next step of the procedure, as shown in FIG. 9F, a silicone tubular sleeve is placed over and extends along the entire jaw ridge line, covering the spheroidal domes and extending substantially up to the locater implants. The silicone sleeve 115, as explained above, has the substantially omega-shaped cross section, providing for a lip 116 at the bottom of the denture to form a seal along the jaw ridge line.

Figure 9G:
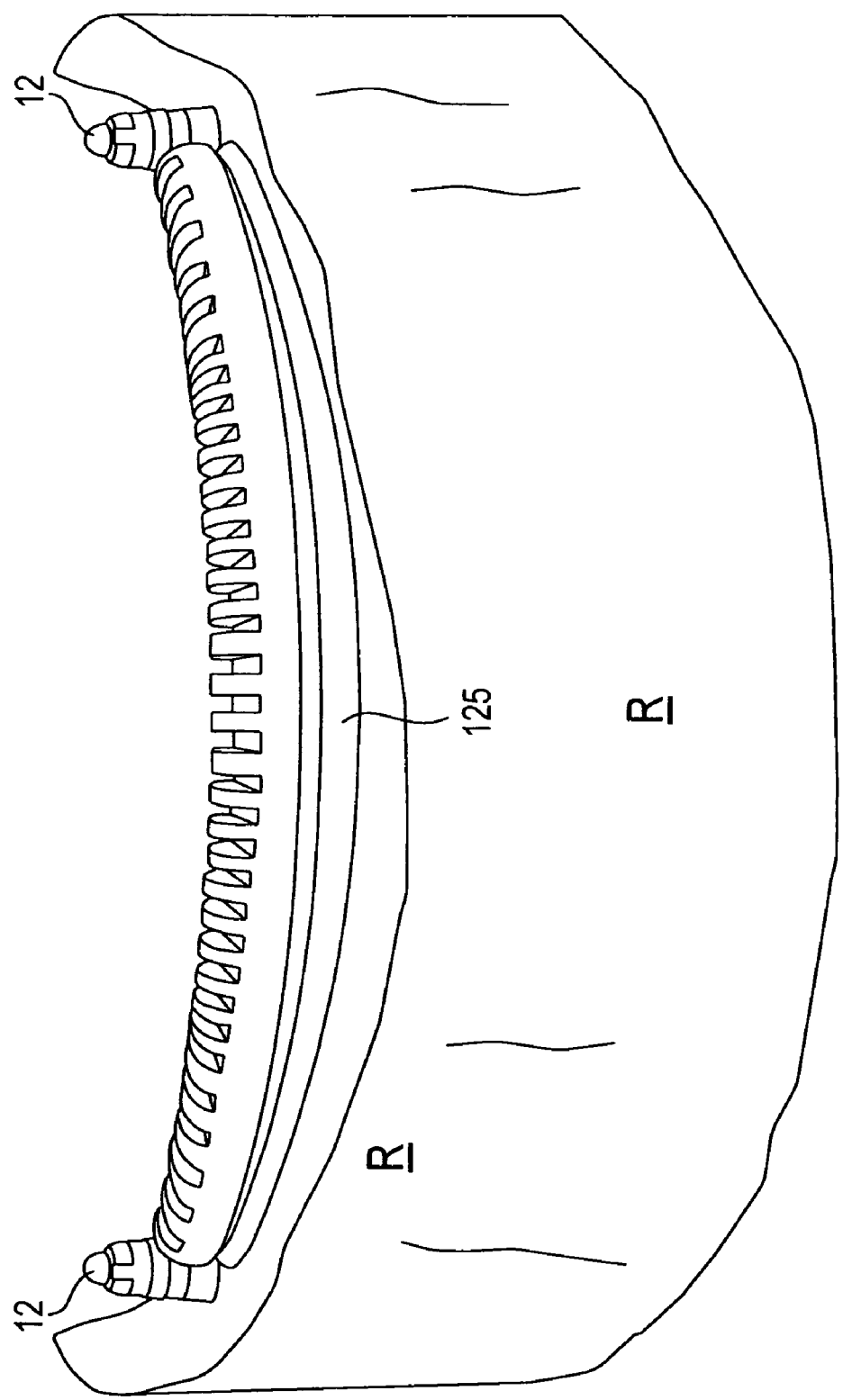

After the silicone sleeve tube 115 is in place, a metal reinforcement frame 125 is placed over the silicone tube (as shown in FIG. 9G). This frame serves as structural reinforcement for the denture to be formed in place over the jaw bone. The metal reinforcement frame 120 has a similar cross section to that of the silicone sleeve tube is placed over the sleeve and extends along and around the substantially full length of the silicone sleeve, in a preferred embodiment. This provides the maximum structural reinforcement of the denture when it is relined in situ.

While the jaw ridge is being prepared, a denture foundation, formed of a relatively hard and strong resin, is being excavated internally so as to generally fit over the frame covering the jaw ridge. The foundation will also have the openings for the locator implants 102. A first soft auto cure resin is placed in the hollowed-out denture foundation and the filled denture is placed over the metal frame. The openings at the posterior-most region of the foundation fits over the locating implants, such that the resin cures around the sleeves covering the locater implants. The soft auto cure resin also flows through the openings in the metal frame and forms around the shape of the ridge of the jaw, as outlined by the omega-shaped silicone sleeve. When the resin is fully cured, the denture foundation is removed from the jaw and the remaining internal space concavity in the denture is defined by the interior of the silicone sleeve 115 to have the omega-shaped cross-section, including edge channels.

Figure 9H:
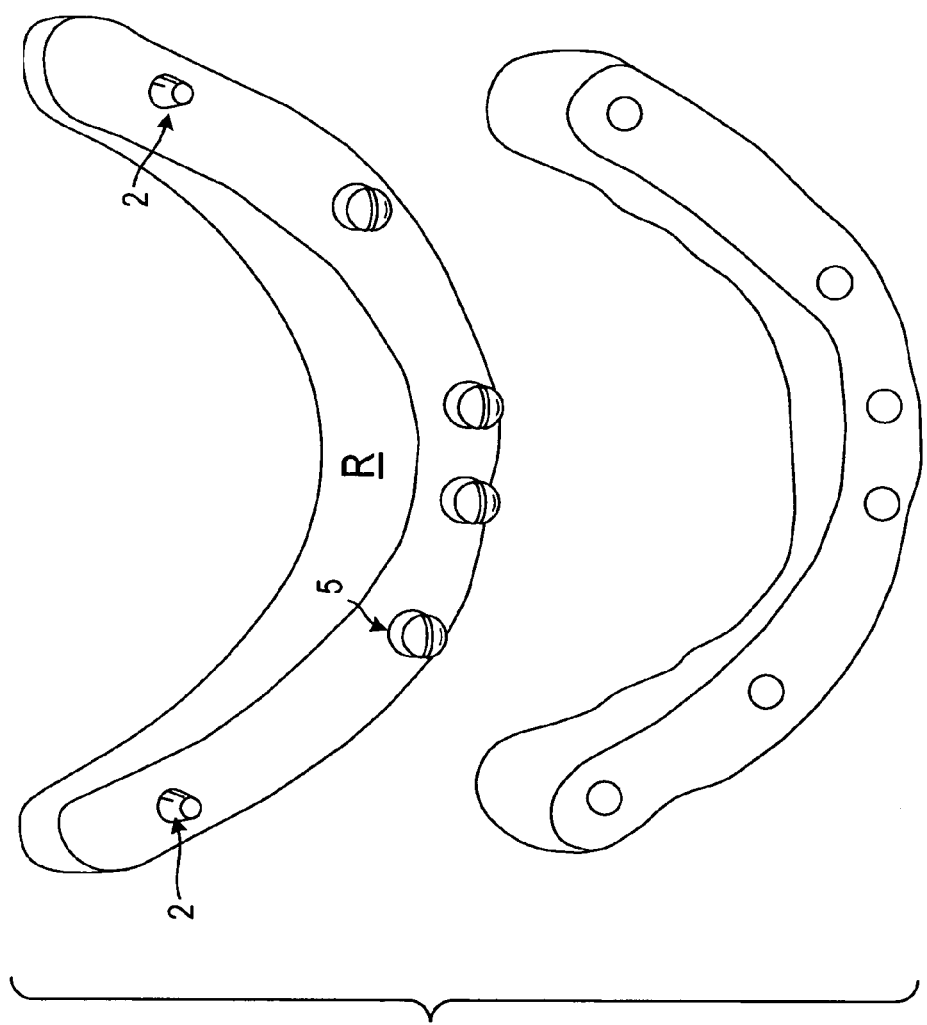
Figure 9I:
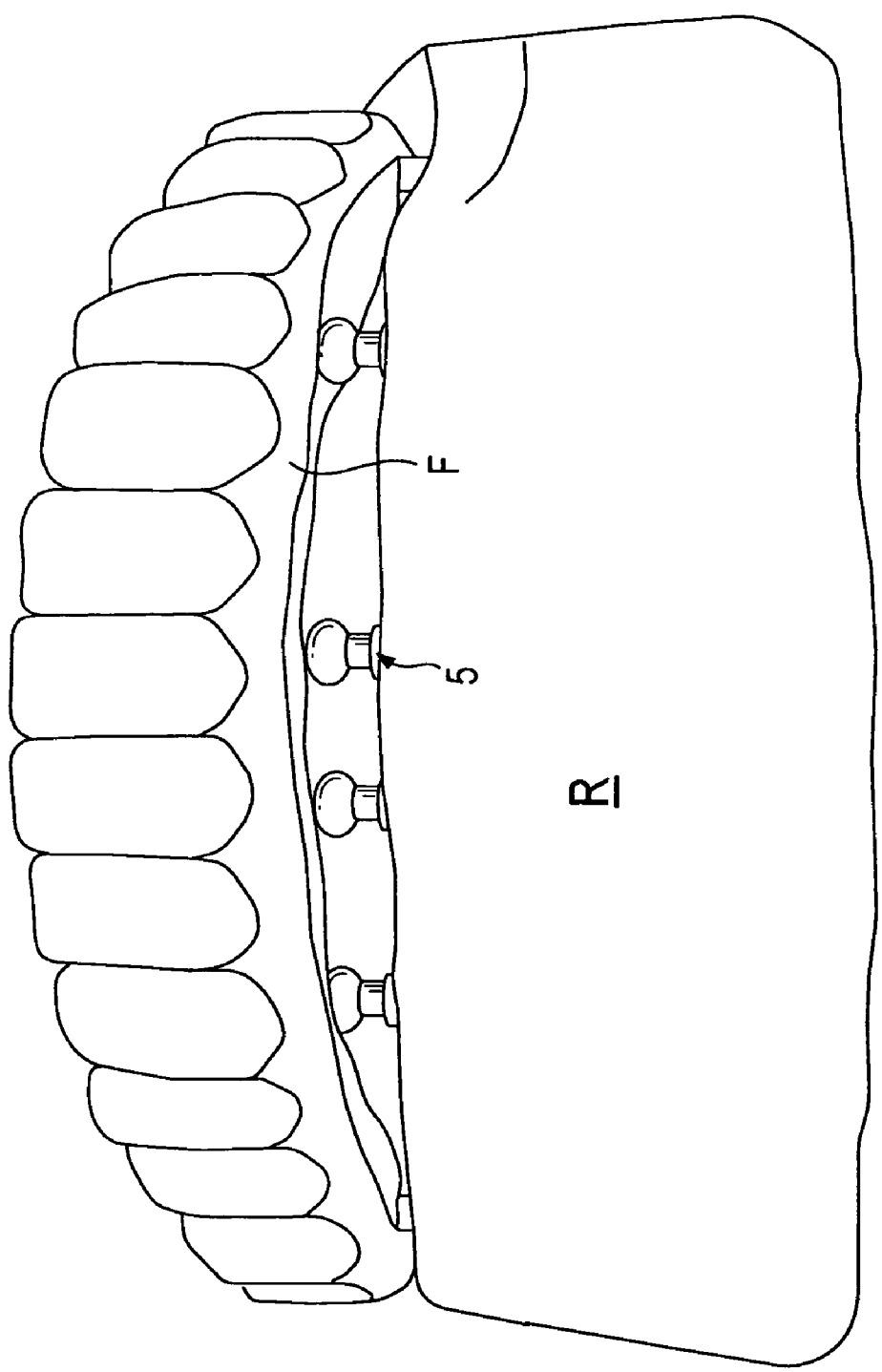

The silicone sleeve 115 is removed, or maintained if desired for further support, and an auto-curing soft liner resin is placed within the previously molded internal space of the denture foundation, including the edge channels. The thus filled denture foundation is again placed over the jaw ridge, and the liner resin permitted to cure, matching the smooth contours of the jaw ridge, and holding the embedded spheroidal heads, and enveloping the neck portions of the holding implants. When fully cured, the liner material holds the spheroidal heads 5, as shown in FIG. 9H, and surrounds at least the base portion of the indexing implants 2, i.e., that closest to the gumline. The highly resilient nature of the liner resin, after curing, permits removing the denture foundation from the jaw ridge by exerting sufficient force. FIG. 9I shows the cured liner material, out of the denture, for purposes of explanation. The soft liner resin can be any dental resin that adheres to the surface of the above first autocured dental resin. Suitable such resins include the known auto-curing silicone dental resin for liners.

The denture foundation can be readily replaced in its precise position in the mouth by inserting the locater implants into the sleeves imbedded in the denture at the posterior regions and then pushing down on the forward portion of the denture such that the spheroid caps pass into the interior of the denture and are held tightly by the lips of the cured flexible resin.

When the denture foundation no longer fits securely, it can be deeply excavated to replace the softer liner resin. It is possible to provide for a greater depth of the flexible soft resin filling, without significantly reducing the structural strength of the hard denture base because of he metal frame embedded within the soft resin immediately adjacent the hard structure. This serves to provide the additional structural strength and rigidity required to maintain the integrity of the denture and to avoid having it come loose by being stretched or warp so as to loose its tight fit with respect to the spheroid caps of the implants.

The distal motion of the denture, namely that portion having the appearance of natural teeth, can be formed in accordance with the usual molding techniques followed by dentists. The prosthetic "teeth" are molded so as to engage complementarily with the opposing natural teeth in the mouth, or with the opposing denture if one was previously emplaced. The use of this invention does not interfere with such conventional molding techniques, and thus allows dentists and dental laboratories to continue with their usual practice when forming a permanent denture prosthesis.

The above disclosure sets forth preferred embodiments of the present invention. Only the following claims fully define the invention:

The following invention is claimed:

1. A method of forming in situ a resiliently lined foundation for a rigid prosthetic denture, the foundation having a concave support undersurface and being of the type removably secured to permanently implanted dental support posts embedded into a patient's jaw, wherein the support posts each include a shank secured to the patient's jaw and a support portion extending outwardly longitudinally and laterally from the shank and beyond the patients jaw surface, and where the concave support undersurface of the denture has substantial space for additional support material to mate with the support portions, the method comprising the steps of:

forming indexing sockets, through the concave support undersurface of the denture foundation, for a series of implanted indexing guide posts, at locations intended to mate with the guide posts when the denture is properly secured in the mouth, the indexing guide posts each having an exposed indexing portion extending beyond the jaw of the patient, each of the indexing sockets having a shape wherein the portions distal from the jaw have smaller cross-sections than the portion adjacent the jaw, but of sufficient size and shape to permit smooth and easy insertion into, and removal from, an indexing socket of at least the outermost exposed indexing portion;

placing portions of curable dental resin material into the concave support undersurface portion of the denture and placing the denture foundation onto a form selected from the group consisting of the patient's jaw bone ridge and a model of the patient's jaw bone ridge, including the dental support posts and indexing posts, to mold the curable resin so that the resin cures to form a tight fit around the jawbone ridge and support posts, and where the cured resin is sufficiently resilient to permit easy manual removal and reinsertion by the patient of the dental prosthesis by mating with the indexing portions;

the dental prosthesis thus being capable of being readily relined with the resilient resin, if needed, by chair side techniques by a dentist, without loss of proper fit and placement.

2. The method of claim 1 further comprising, prior to placing the curable resin-filled denture foundation onto the form, placing over the support portions of the dental posts a flexible open tubular covering, which extends over and around all of the support portions, the opening of the tubular covering extending along the full length of the tubular covering and being defined by opposed longitudinal edges, wherein the longitudinal edges of the tubular covering are placed in contact with the sides of the jawbone ridge, removing the denture foundation from the mold after the auto-curing resin has cured and placing a second portion of soft auto-curing resin into the remaining cavity defined by the tubular covering and replacing the refilled foundation onto the form so that the resin cures to form the tight fit.

3. The method of claim 2 where each implanted support post comprises a platform at the surface of the jaw ridge, a relatively large diameter flattened spheroidal top portion having a relatively large diameter transverse to the longitudinal axis of the post, and a relatively slender neck portion intermediate the spheroidal top and the platform.

4. The method of claim 3, wherein the tubular covering has an omega-shaped cross-section along an axis parallel to the support posts.

5. The method of claim 4 wherein the tubular covering is formed of a material which is non-adherent to the curable dental resin.

6. The method of claim 3, further comprising applying removable resilient bands, prior to curing the resin, to the necks of the support posts to vary the stress required to remove the finished denture from the patient's mouth.

7. The method of claim 2, further comprising placing an open reinforcement tube within the concave undersurface so that it is held within the resilient resin while it is curing, to reinforce the structure of the foundation.

8. The method of claim 1 further wherein durable inserts are secured into the indexing sockets of the denture foundation prior to placing the curable resin-filled denture foundation onto the form, the inserts mating with the indexing posts when the denture foundation is placed thereover, so that the inserts are retained in place by the cured resin.

9. The method of claim 1, wherein the exposed indexing post portions have a shape intended to mate with the indexing sockets, wherein the portions distal from the jaw have progressively smaller cross-sections.

10. A rigid prosthetic denture foundation, of the type removably securable to permanently implanted dental support posts embedded into a patient's jaw, where the support posts each include a shank secured to the patient's jaw and a support portion extending outwardly longitudinally and laterally from the shank and beyond the patients jaw surface, the denture foundation having a concave support undersurface, the improvement comprising:

a plurality of indexing sockets formed through the denture foundation for holding indexing implants, each socket having a smaller cross-section distally outwardly from the support undersurface, placed at locations intended to mate with implanted indexing posts, when the denture is properly placed in the mouth, the indexing posts having exposed indexing portions extending outwardly from the jaw;

a resilient foundation liner formed in situ of a resilient resin within the concave portion, the resilient liner defining at least one support socket sized and shaped to firmly grip the support portion of each support post and to have opposing longitudinal edges intended to rest upon the gum ridge in the patient's jaw;

the denture foundation thereby being readily relined by chair side techniques by a dentist, without loss of proper fit and placement.

11. The denture foundation of claim 10 wherein the indexing sockets are defined by inserts of rigid structural material secured into each socket and embedded in the resilient resin; the shape of the indexing sockets being such as to snugly, but not firmly, surround the indexing portion of the indexing implants, so that the foundation is easily movable longitudinally relative to the indexing implants, the indexing portion and mating indexing socket having a smaller cross-section distally outwardly from the gum ridge of the jaw.

12. The denture foundation of claim 11 wherein the inserts in the indexing sockets are formed of a metal.

13. The foundation of claim 12, wherein the inserts in the indexing sockets are formed of a metal.

14. The denture foundation of claim 10 wherein the support posts have a spheroidal top portion having a spherical major diameter transverse to the axis of the post, and a relatively narrow neck portion supporting the spheroidal top portion above the gum, and wherein the resilient liner support sockets have an opening matching the neck portion of the support post and an inner spheroidal chamber having a major spherical diameter substantially the same as the spherical top of the support posts.

15. The denture foundation of claim 10 further comprising a reinforcing framework, of a relatively hard and rigid material, embedded in the resilient resin as a structural reinforcement.

16. The denture foundation of claim 15, wherein the reinforcing framework is formed of a metal.

17. The denture foundation of claim 10 wherein the longitudinal edges of the cured resilient resin are in the form of a pair of lips, designed to form a seal along the gum ridge surface, the pair of lips being formed in situ, during the preparation of the foundation.

18. The denture foundation of claim 10 wherein the resilient liner support sockets have a relatively narrow opening and a wider inner spheroidal chamber, the widths of the opening and inner chamber matching the neck portion and spheroidal top portion of the support posts, respectively.

19. A dental support implant for being implanted into the jawbone comprising:
 a shaft having a first threaded end portion adapted to anchor the shaft into rigid dental material selected from the group consisting of tooth stubs and bone matrix;
 a prosthesis engaging member portion for engaging a dental prosthesis after the shaft is anchored into the rigid dental material, the prosthesis engaging member comprising a flattened spheroidal portion, having a major spherical diameter transverse to the axis of the implant, the spheroidal portion also defining a slot for connecting to a driving tool for driving the screw end into the rigid dental material, the slot extending parallel to the minor diameter of the spheroidal portion, substantially parallel to the axis of the shaft of the implant;
 a flange member extending transversely from the proximal end of the shaft, and having a substantially smooth and circular circumference and a substantially flat surface facing towards the spheroidal portion; and
 a neck portion, located intermediate the flange and the spheroidal portion, having a diameter smaller than each of the major spherical diameter of the spheroidal portion and the diameter of the flange.

20. A method of forming in situ a resiliently lined foundation for a rigid prosthetic denture, the foundation having a concave support undersurface and being of the type removably secured to permanently implanted dental support posts embedded into a patient's jaw, wherein the support posts each include a shank secured to the patient's jaw and a support portion extending outwardly longitudinally and laterally from the shank and beyond the patients jaw surface, and where the concave support undersurface of the denture has substantial space for additional support material to mate with the support portions, the method comprising the steps of:
 placing portions of auto-curing dental resin material into the concave support undersurface portion of the denture and placing the auto-curing resin-containing denture foundation onto a form selected from the group consisting of the patient's jaw bone ridge and a model of the patient's jaw bone ridge, including the dental support posts and indexing posts, to mold the curable resin so that the resin cures to form a tight fit around the jawbone ridge and support posts, and where the cured resin is sufficiently resilient to permit easy manual removal and reinsertion by the patient of the dental prosthesis; and
 further comprising placing a resilient silicone jacket covering the support portion of each support post prior to placing the auto-curing resin-containing denture foundation onto the form, and allowing the resin to cure, such that the auto-cured resin does not adhere to the support posts and the silicone jackets are held within the cured resin material;
 the dental prosthesis thus being readily relined if needed, by chair side techniques by a dentist, without loss of proper fit and placement.

21. A resiliently lined foundation for a rigid prosthetic denture, the foundation having a concave support undersurface and being of the type removably securable to permanently implanted dental support posts embedded into a patient's jaw, wherein the support posts each include a shank secured to the patient's jaw and a support portion extending outwardly longitudinally and laterally from the shank and beyond the patients jaw surface, and where the concave support undersurface of the denture has substantial space for additional support material to mate with the support portions, the foundation comprising:
 an auto-cured resin-containing denture foundation formed in situ over a form selected from the group consisting of the patient's jaw bone ridge and a model of the patient's jaw bone ridge, including the dental support posts, so that the auto-cured resin forms a tight fit around the jawbone ridge and support posts, and where the cured resin is sufficiently resilient to permit easy manual removal and reinsertion by the patient of the dental prosthesis;
 the auto-cured resin further comprising, opposed longitudinal edges, wherein the longitudinal edges of the foundation are intended to be in close contact with the sides of the jawbone ridge, and
 further comprising resilient silicone jackets held within the resilient in situ cured material and intended to fit over the support portion of each support post to provide further durability when removing and reattaching the denture to the jaw ridge; the dental prosthesis thus being more durable as well as more readily relined if needed, by chair side techniques by a dentist, without loss of proper fit and placement.

* * * * *